US008704171B2

(12) United States Patent
Robinson et al.

(10) Patent No.: US 8,704,171 B2
(45) Date of Patent: Apr. 22, 2014

(54) CHEMICAL IONIZATION REACTION OR PROTON TRANSFER REACTION MASS SPECTROMETRY

(71) Applicant: MKS Instruments, Inc., Andover, MA (US)

(72) Inventors: Timothy Roger Robinson, Burland (GB); Mark Attwood, Cupertino, CA (US); Xing Chen, Lexington, MA (US); William M. Holber, Winchester, MA (US); Mark Philip Longson, Waterhouses (GB); Jonathan Henry Palk, Sandbach (GB); Ali Shajii, Canton, MA (US); John A. Smith, North Andover, MA (US)

(73) Assignee: MKS Instruments, Inc., Andover, MA (US)

( * ) Notice: Subject to any disclaimer, the term of this patent is extended or adjusted under 35 U.S.C. 154(b) by 0 days.

(21) Appl. No.: 13/682,379

(22) Filed: Nov. 20, 2012

(65) Prior Publication Data

US 2013/0203180 A1 Aug. 8, 2013

Related U.S. Application Data

(63) Continuation of application No. 12/026,799, filed on Feb. 6, 2008, now Pat. No. 8,334,505, which is a continuation-in-part of application No. 11/869,978, filed on Oct. 10, 2007, now Pat. No. 8,003,935.

(51) Int. Cl.
*G01N 27/62* (2006.01)
(52) U.S. Cl.
USPC ........... 250/288; 250/281; 250/282; 250/283; 250/423 R; 250/424

(58) Field of Classification Search
USPC .............. 250/281, 282, 283, 288, 423 R, 424
See application file for complete search history.

(56) References Cited

U.S. PATENT DOCUMENTS

| 3,555,272 A | 1/1971 | Munson et al. |
| 4,122,343 A | 10/1978 | Risby et al. |

(Continued)

FOREIGN PATENT DOCUMENTS

| JP | S51-088286 | 8/1976 |
| JP | S55-12632 | 1/1980 |

(Continued)

OTHER PUBLICATIONS

Moni et al., "Atmospheric Pressure Microwave Induced Plasma Ionization Source for Molecular Mass Spectrometry", American Society for Mass Spectrometry, pp. 42-49, 1998.*

*Primary Examiner* — Michael Logie
(74) *Attorney, Agent, or Firm* — Proskauer Rose LLP

(57) ABSTRACT

A system and methods are described for generating reagent ions and product ions for use in a mass spectrometry system. Applications for the system and method are also disclosed for detecting volatile organic compounds in trace concentrations. A microwave or high-frequency RF energy source ionizes particles of a reagent vapor to form reagent ions. The reagent ions enter a chamber, such as a drift chamber, to interact with a fluid sample. An electric field directs the reagent ions and facilitates an interaction with the fluid sample to form product ions. The reagent ions and product ions then exit the chamber under the influence of an electric field for detection by a mass spectrometer module. The system includes various control modules for setting values of system parameters and analysis modules for detection of mass and peak intensity values for ion species during spectrometry and faults within the system.

11 Claims, 6 Drawing Sheets

(56) References Cited

U.S. PATENT DOCUMENTS

| | | | |
|---|---|---|---|
| 8,003,935 B2 * | 8/2011 | Robinson et al. | 250/288 |
| 8,003,936 B2 * | 8/2011 | Robinson et al. | 250/288 |
| 8,334,505 B2 * | 12/2012 | Robinson et al. | 250/288 |
| 2002/0125423 A1 * | 9/2002 | Ebeling et al. | 250/288 |
| 2003/0020011 A1 * | 1/2003 | Anderson et al. | 250/287 |
| 2006/0022132 A1 * | 2/2006 | Zhang | 250/290 |
| 2006/0266102 A1 * | 11/2006 | Tolliver | 73/23.2 |
| 2006/0278824 A1 * | 12/2006 | Truche et al. | 250/288 |
| 2007/0102634 A1 * | 5/2007 | Frey et al. | 250/288 |
| 2008/0236249 A1 * | 10/2008 | Fernandez de la Mora | 73/23.35 |

FOREIGN PATENT DOCUMENTS

| | | |
|---|---|---|
| JP | S62-013625 | 1/1987 |
| JP | S64-007466 | 1/1989 |
| JP | 2746887 | 2/1998 |
| JP | 2003-194723 A | 12/2001 |

\* cited by examiner

# CHEMICAL IONIZATION REACTION OR PROTON TRANSFER REACTION MASS SPECTROMETRY

RELATED APPLICATIONS

This application is a continuation of U.S. patent application Ser. No. 12/026,799 filed on Feb. 6, 2008, which is a continuation-in-part of U.S. patent application Ser. No. 11/869,978 filed on Oct. 10, 2007, now U.S. Pat. No. 8,003, 935 issued on Aug. 23, 2011, both of which are owned by the assignee of the instant application and the entire disclosures of which are incorporated by reference herein. U.S. patent application Ser. No. 11/869,980 filed on Oct. 10, 2007, now U.S. Pat. No. 8,003,936 issued on Aug. 23, 2011, is also owned by the assignee of the instant application and incorporated herein by reference in its entirety.

TECHNICAL FIELD

The invention relates generally to mass spectrometry and in particular to mass spectrometry in which reagent ions are formed using a microwave or high-frequency radio frequency plasma, and applications therefor.

BACKGROUND

Mass spectrometry generally refers to the direct measurement of the value of a particle's mass or an implicit determination of the value of the particle's mass by measurement of other physical quantities using spectral data. Mass spectrometry often involves determining the mass-to-charge ratio of an ionized molecule or component. When the charge of the ionized particle is known, the mass value of the particle can be determined from a spectrum of mass values.

Systems for performing mass spectrometry are known as mass spectrometers. Mass spectrometer systems generally include an ion source, a mass filter or separator, and a detector. For example, a sample of molecules or components can be ionized by electron impact in the ion source to create ions. Ions having different mass values are separated by the mass analyzer into a mass distribution or spectrum, for example, by application of electrical or magnetic fields to the ions. The detector collects the ions, and the mass distribution may be viewed and/or recorded. The relative abundance of mass values in the spectrum is used to determine the composition of the sample and the mass values or identities of molecules or components of the sample.

Many different types of mass spectrometer exist, including a category referred to as ion-molecule reaction mass spectrometers (IMR-MS). Within this category, several technologies exist including proton transfer reaction mass spectrometry (PTR-MS) and selected ion flow tube mass spectrometry (SIFT-MS). Such categories generally refer to the method by which ions are generated. For example, proton transfer reaction mass spectrometers include an ion source that generates reagent ions, typically hydronium ions ($H_3O^+$), to transfer charge to sample components, e.g., by proton transfer. In selected ion flow tube mass spectrometers, a carrier gas transports filtered ions along a flow tube. In proton transfer reaction mass spectrometers sold by Ionicon Analytik GmbH of Innsbruck, Austria, a hollow cathode tube is used as an ion source to produce reagent ions by applying a DC plasma discharge to a stream of water vapor.

Some mass spectrometry systems are classified by the type of mass analyzer used. For example, some mass spectrometry systems are based on "tandem techniques" where another analytical technology is used in combination with mass spectrometry equipment. An example is gas chromatography mass spectrometry (GC-MS) where a gas chromatography column is used to separate components of a sample prior to analysis with a mass spectrometer.

Mass spectrometry can be used to determine the quantities of volatile organic compounds (VOCs) in a sample. Measurement of VOCs has become important because the presence of VOCs, even in trace quantities, can serve as an important diagnostic indicator in many different applications and may affect human health. For example, when the concentration of VOCs rises above a certain level, detrimental health effects can occur in humans such as respiratory conditions. Moreover, the type and quantities of VOCs in a particular sample can be indicative of the presence of explosives, harmful chemical agents, combustion products, disease agents, decay or contamination, arson accelerants, or drugs of abuse. Additionally, monitoring the presence and quantity of VOCs is useful in industrial processing, such as biochemical or pharmaceutical manufacturing processes.

Several drawbacks are inherent with existing mass spectrometry systems both generally and as applied to detection of VOCs. For example, mass spectrometry systems employing gas chromatography are not suitable for continuous, real-time monitoring of a fluid sample due to the relatively slow analysis of a sample. Moreover, previous mass spectrometry systems often require collection of a sample from the field prior to analysis of the sample in a lab-based environment, rather than in situ analysis. Previous mass spectrometry systems are relatively insensitive to lower-concentration components in a sample, for example, because ion sources do not produce a sufficient quantity of ions to generate an identifiable mass spectrum for lower-concentration constituents. The mass spectrum for lower-concentration constituents in such systems is often indistinguishable from noise due to dynamic range limitations or overwhelmed by peak interference from higher-concentration components or noise generated by electronic or mechanical equipment. Mass spectrometry systems with suitable levels of sensitivity can facilitate detection of the existence of VOCs, but may be subject to interference from other compounds present and therefore unable to positively identify a particular compound or species.

SUMMARY

There is a need for a robust mass spectrometry system that can provide continuous, real-time, and in situ analysis. Moreover, there is a need for a system that can reliably determine the existence and identification of VOCs in a particular sample, including trace quantities of VOCs.

Systems and methods that embody the invention feature mass spectrometry that uses microwave energy or high-frequency RF energy to produce reagent ions, for example, hydronium ions, for interacting with a fluid sample. The use of microwave energy has been found to generate reagent ions, such as hydronium, in greater quantities than other reported ionization methods (e.g., where a radioactive source is used) while also avoiding electrode erosion and instability associated with DC discharge sources. A greater quantity of reagent ions results in enhanced system sensitivity, facilitating the quantitative measurement and/or identification of individual VOCs, even in trace quantities. High-frequency RF energy also demonstrates similar advantages in mass spectrometry to those achieved when using microwave energy to generate reagent ions. Moreover, the invention relates to systems and methods for real-time measurement of VOCs at relatively high pressures, e.g., more than about 100 millibar (about 10,000 Pascals).

Systems and methods that embody the invention, in some embodiments, can be used to detect VOCs in concentrations on the order of parts-per-trillion by volume (pptV). In some embodiments, a module analyzes and classifies a particular detected VOC based on the acquired mass spectrum. The system components used in embodiments of the invention are suitable for portable mass spectrometry and/or in situ applications. The concepts described herein can be used in mass spectrometry systems employing chemical ionization reaction mass spectrometry (CIRMS) techniques or proton transfer reaction mass spectrometry (PTR-MS) techniques.

In some embodiments, the invention includes analysis or control modules for processing data acquired, detected, or collected during system operation. For example, some systems include a multivariate analysis module to facilitate detection and identification of VOCs based on the mass spectrum. The multivariate analysis module can also be used for monitoring the mass spectrometry system or detecting a fault within the system. Additionally, a control module or feedback loop can be used to control generation of reagent ions and sample ions and their throughput in mass spectrometry systems, for example, by controlling various process parameters of the system. Such parameters include various electrical fields, pressure values, ion and vapor flow rates and ion energies. The invention also relates to couplings, connections, or interfaces between various system components for influencing the movement of reagent ions, sample components, and product ions through mass spectrometry systems.

Sensitivity of the chemical ionization reaction mass spectrometers and proton transfer reaction mass spectrometers described herein can be altered based on a variety of system parameters. Sensitivity can be altered based on reagent ion concentration in the drift region (e.g., hydronium ion concentration).

The ratio E/N (expressed in Townsends (Td)) of the electric field to the concentration of neutral particles in the drift region can affect the sensitivity of the spectrometers. The E/N ratio is a function of pressure (e.g., gas density) and electrical field intensity in the drift region. The E/N ratio affects the time required for ions to traverse the drift region.

Sensitivity can be affected by the intensity of the ion beam reaching the mass spectrometer after exiting the drift region (consisting of reagent ions and product ions). This is a function of the transfer optics (e.g., electrode/lens aperture geometry), electrical fields and pressure regimes (pumping) in the transfer region which impact beam focusing and beam transmission properties.

Sensitivity can be altered based on the ratio between partial pressures of bulk sample gas and neutral reagent species in the drift region. The proton transfer rate constant (k) for the gas sample species being monitored affects sensitivity. The length of the drift region affects the sensitivity because a longer drift region requires more time for substances to traverse the drift region, and therefore the opportunity for reagent ions and sample species to react. Sensitivity also can be affected by various mass spectrometer related sensitivity factors (e.g., ion transmission/mass discrimination, detector/preamplifier gain and the signal to noise ratio)

The invention, in one aspect, relates to a system. The system includes a microwave or high-frequency RF energy source to ionize particles of a reagent vapor with microwave or RF energy to form one or more reagent ions. The system also includes a chamber including an inlet port that allows a sample to enter the chamber to interact with the one or more reagent ions from the microwave or high-frequency RF energy source to form one or more product ions. The chamber has an electromagnetic field generated therein. The system also includes a quadrupole mass spectrometer module disposed relative to an exit orifice of the chamber to collect the one or more product ions and the one or more reagent ions to facilitate a determination of a value for a peak intensity and/or mass of each of the product ions and reagent ions.

In some embodiments, the microwave energy source includes a microwave plasma generator. The high-frequency RF energy source can include a capacitively-coupled RF plasma generator. In some embodiments, the reagent ions include hydronium ions, oxygen ions, or nitrous oxide ions. The sample can include one or more volatile organic compounds (VOCs).

Some embodiments of the system feature a set of electrodes disposed relative to the chamber to generate the electromagnetic field in the chamber. The electromagnetic field facilitates an interaction between the reagent ions and the sample and directs the product ions and reagent ions through the exit orifice of the chamber. The set of electrodes can be radially disposed about an axis of the chamber, and the electromagnetic field directs the product ions and reagent ions substantially axially. In some embodiments, a control module is in communication with the set of electrodes. The control module is operable to determine a value of the electromagnetic field (or electromagnetic field gradient) within the chamber based on an operating parameter of the system.

The system can include a mass flow controller, a capillary tube, or a leak valve for determining an amount of the sample that enters the chamber. The system can include a mass filter disposed between the microwave or high-frequency RF energy source and the chamber to selectively allow reagent ions to pass into the chamber. Examples of a suitable mass filter include a quadrupole mass filter. In some embodiments, the system includes a multivariate analysis module in communication with the system that is operable to analyze data from the quadrupole mass spectrometer module.

The microwave energy source can include a microwave generator, a resonator portion, a tube portion disposed within the resonator portion and in communication with the chamber and one or more chokes through which the tube passes to reduce an amount of microwave energy within a reagent vapor supply, the chamber, or both. In some embodiments, the system includes a control module in communication with the system that is operable to change an input parameter of the system based in part on an operating parameter of the system. Such parameters include a composition of the sample, a pressure of the chamber, a speed of the product ions or reagent ions through the chamber, a rate of flow of the sample or reagent ions into the chamber, an energy of the product or reagent ions, the chemical composition of the reagent ions, product ions, or the sample, or any combination thereof. In some embodiments, the control module is operable to change an input parameter of a set of electrodes that generate the electromagnetic field within the chamber based in part on the operating parameter.

In some embodiments, the system includes a control module in communication with the system to detect or identify a fault in an operating parameter of the system. The control module can also change a value of the operating parameter based in part on the detection or identification of the fault. The system can include a control module in communication with the system for monitoring the system. The control module sets or adjusts a value of an operating parameter of the system in response to the monitoring and the control module is based on a multivariate statistical analysis algorithm. In some embodiments, the control module includes a multivariate statistical analysis module. The multivariate statistical analysis module can be used for process monitoring and/or to detect a fault in the mass spectrometry system. The multivariate statistical analysis module can be used to detect and/or identify faults. In some embodiments, the multivariate statistical analysis module is used to interpret mass spectroscopy data (e.g., in a mass spectrum) and be used to identify components from constituent peaks in the mass spectrum. The multivariate statistical analysis module can be used with a quadrupole mass spectrometer or a time-of-flight mass spectrometer. In some embodiments, a control module or a multivariate statistical analysis module is used both to detect and/or identify faults in the system and to interpret and/or analyze data, for example, to identify components from constituent peaks in the mass spectrometer.

The system can also include an extraction electrode disposed relative to the chamber. The extraction electrode defines an orifice through which reagent ions or product ions pass to the quadrupole mass spectrometer module. The extraction electrode is also operable to specify an energy value of the reagent ions or product ions for collection by the quadrupole mass spectrometer module. Some embodiments of the system feature a lens assembly disposed relative to the chamber for focusing the reagent ions and product ions on an extraction orifice that facilitates passage of reagent ions and product ions to the mass spectrometer module.

In another aspect, the invention relates to a method for generating one or more reagent ions for a proton transfer reaction mass spectrometer or chemical ionization reaction mass spectrometer. The method involves supplying a reagent vapor and providing microwave energy to the reagent vapor to generate one or more reagent ions.

The method can also involve directing the one or more reagent ions to a region for interacting with constituents of a sample to form product ions. The reagent ions can be generated by a microwave plasma. The reagent vapor can include water vapor, oxygen, or nitrous oxide, and the reagent ions can be hydronium ions, oxygen ions, or nitrous oxide ions. In some embodiments, the microwave energy is provided by electromagnetic waves or radiation having a frequency greater than about 800 MHz.

The invention, in another aspect, relates to a method for generating one or more reagent ions for a proton transfer reaction mass spectrometer or chemical ionization reaction mass spectrometer. The method involves supplying a reagent vapor and providing high-frequency RF energy to the reagent vapor to generate the reagent ions.

In some embodiments, the RF energy is provided by electromagnetic waves having a frequency between about 400 kHz and about 800 MHz. The reagent ions can be generated by a capacitively-coupled RF plasma.

In another aspect, the invention relates to a method. The method involves supplying a reagent vapor to a plasma region and providing microwave or high-frequency RF energy to the reagent vapor in the plasma region to form one or more reagent ions. The method involves interacting the reagent ions with a gas sample to generate one or more product ions. The method also involves directing the product and reagent ions to a collector region of a quadrupole mass spectrometer module and determining, by the mass spectrometer module, a value for a peak intensity and/or mass of the product ions and reagent ions.

Another aspect of the invention relates to a mass spectrometry system. The mass spectrometry system includes a means for generating one or more reagent ions from a reagent vapor supply by providing the reagent vapor with microwave or high-frequency RF energy. The system also includes a means for interacting a sample with the reagent ions to form one or more product ions. The system includes a means, which includes an electromagnetic field, for directing the product ions and reagent ions to a collector region. The system also includes a means in communication with the collector region for determining a value for a peak intensity and/or mass of each of the product ions and reagent ions.

The invention, in one aspect, relates to a system. The system includes a microwave or high-frequency RF energy source to ionize particles of a reagent vapor with microwave or RF energy to form one or more reagent ions. The system also includes a chamber including an inlet port that allows a sample to enter the chamber to interact with the reagent ions from the microwave or RF energy source to form one or more product ions. The system also includes a mass spectrometer module disposed relative to an exit orifice of the chamber. The mass spectrometer module includes a flight region through which the product ions or reagent ions travel and which defines a path length. The mass spectrometer module also includes a collector region to receive the product ions or reagent ions from the flight region. A value for a mass of the product ions or reagent ions is determined based on an amount of time over which each of the product ions and reagent ions traverses the path length.

In some embodiments, the mass spectrometer module also includes an ion beam adjuster disposed relative to the exit orifice of the chamber to pulse a flow of the product ions and reagent ions into the flight region. The mass spectrometer module also includes an optical system disposed in the flight region to increase a value of the path length traveled by the product ions and reagent ions. The ion beam adjuster can modulate the flow of the product ions and reagent ions by a pseudo random binary sequence provided from a controller. In some embodiments, an analysis module performs a maximum likelihood signal processing algorithm on data received from the mass spectrometer module to determine the value of a peak intensity and/or mass of the product ions and reagent ions. The analysis module can deconvolute data received from the mass spectrometer module to determine the value for the peak intensity and/or mass of the product ions or reagent ions. The collector region can include a stacked micro-channel plate detector operating in pulse counting mode or a bi-polar detector. In some embodiments, the optical system includes a reflectron. The system can feature a lens to focus the reagent and product ions onto the ion beam adjuster, and the ion beam adjuster includes an ion beam chopper, an ion beam gate, an ion beam modulator, Bradbury-Nielsen gate, or any combination of these.

The system also features, in some embodiments, an optical system disposed relative to the chamber and the mass spectrometer module. The optical system includes at least one quadrupole lens to direct a flow of the reagent ions and product ions toward an ion beam adjuster. In some embodiments, the mass spectrometer module defines a substantially linear axis through the flight region. The substantially linear axis can be substantially parallel to a second axis passing through the flight region (e.g., a Uthoff trajectory).

In some embodiments, the system includes a mass filter disposed relative to the microwave energy source and the chamber to selectively allow a subset of the reagent ions to enter the chamber. The filter can be a quadrupole mass filter. The system can feature an analysis module to receive data from the mass spectrometer module to interpret data in a mass spectrum including the values for the peak intensity and/or mass of the product ions and reagent ions. The analysis module can be used to detect and/or identify a fault in the mass spectrometry system. The analysis module can be based on a multivariate statistical analysis.

The system features, in some embodiments, a multivariate statistical analysis module to identify components of the sample based on a mass spectrum generated by the mass spectrometer module. The system can include a control module in communication with the system that is operable to detect or identify a fault in the system based on an operating parameter of the system. The control module can change a value of the operating parameter based in part on the detection or identification of the fault.

The system can include a control module in communication with the system to change a value of an input parameter of the system based on an operating parameter of the system. In some embodiments, the system includes a set of electrodes disposed relative to the chamber to create a field for facilitating an interaction between the reagent ions and the sample and to direct the product ions and reagent ions through the exit orifice of the chamber. Such a system can feature a control module in communication with the set of electrodes to determine a value of the field within the chamber based on an operating parameter of the system. The operating parameter of the system can include composition of the sample, pressure of the chamber, speed of the product ions or reagent ions through the chamber, rate of flow of the sample or reagent ions into the chamber, an energy of the product ions or reagent ions, the chemical composition of the product ions, reagent ions, or the sample, or any combination of these. The control module is also operable to change an input parameter of the set of electrodes based in part on the operating parameter.

In another aspect, the invention relates to a system. The system includes a microwave or high-frequency RF energy source to ionize particles of a reagent vapor with microwave or RF energy to form one or more reagent ions. The system includes a chamber including an inlet port allowing a sample to enter the chamber to interact with the reagent ions from the microwave or RF energy source to form one or more product ions. The system also includes a time-of-flight mass spectrometer module disposed relative to an exit orifice of the chamber to generate a spectrum including a value for a mass of the product ions and reagent ions based on an amount of time over which each of the product ions and reagent ions traverses the mass spectrometer.

The time-of-flight mass spectrometer module, in some embodiments, includes a flight region through which the product and reagent ions travel. The flight region defines a path length. The time-of-flight mass spectrometer module also includes an ion beam adjuster to modulate a flow of reagent or product ions into the flight region and an optical system disposed in the flight region to increase the path length traveled by the product ions and reagent ions. The spectrometer module also includes a collector to receive the product ions and reagent ions from the flight region.

In another aspect, the invention relates to a method for processing signals in a time-of-flight mass spectrometer. The signals are based on one or more reagent ions that are generated by providing microwave or RF energy to a reagent vapor and also based on one or more product ions generated by interacting the reagent ions with a fluid sample in an electromagnetic field. The method involves establishing a first flow of ions that includes the reagent ions and product ions and altering the first flow of ions to generate a second flow of ions according to a specified flow pattern. The method also involves receiving the second flow of ions at a detector and determining a mass spectrum from data communicated by the detector according to a maximum likelihood-type statistical algorithm. The mass spectrum includes data indicative of the mass and/or peak intensity of the reagent ions and product ions.

In some embodiments, the second flow is a pulsed flow. The pulsed flow can be based on the specified flow pattern being generated according to a pseudo random binary sequence.

The invention relates to, in another aspect, a method. The method involves supplying a reagent vapor to a plasma region and providing microwave or high-frequency RF energy to the reagent vapor in the plasma region to form one or more reagent ions. The method also involves interacting the reagent ions with a gas sample to generate one or more product ions. The method involves directing the product ions and reagent ions along a trajectory in a flight region of a time-of-flight mass spectrometer module. The method also involves determining, by the mass spectrometer module, a value for a peak intensity and/or mass of the product ions and reagent ions.

An aspect of the invention relates to a system for measuring the mass of one or more reagent ions and one or more product ions. The reagent ions are generated by providing microwave or RF energy to a reagent vapor. The product ions are generated by interacting the one or more reagent ions with a fluid sample in an electromagnetic field. The system includes a set of quadrupole lenses disposed relative to an ion exit orifice of a drift tube assembly for receiving a first flow of ions that includes the reagent ions and product ions. The set of lenses receives the product ions and reagent ions through the exit orifice and creates a second flow of ions directed to an ion beam adjuster. The system also includes the ion beam adjuster, which is operable to selectively allow the second flow of ions to pass to a flight region of a time-of-flight mass spectrometer.

In another aspect, the invention relates to a system. The system includes a means for ionizing particles of a reagent vapor with microwave or high-frequency RF energy to form one or more reagent ions. The system also includes a means, which includes an electromagnetic field, for interacting a sample with the reagent ions to form one or more product ions. The system also includes a means for determining a value for a peak intensity and/or mass of each of the product ions and reagent ions based on an amount of time over which the product ions and reagent ions traverses a specified distance.

The invention, in another aspect, relates to a system for measuring the mass of one or more reagent ions and one or more product ions. The reagent ions are generated by providing microwave or RF energy to a reagent vapor. The product ions are generated by interacting the reagent ions with a fluid sample in an electromagnetic field. The system includes a means for establishing a first flow of ions that includes the reagent ions and product ions. The system also includes a means for modulating the first flow of ions according to a specified interruption pattern to produce a second flow of ions. The system also includes a means for generating a mass spectrum from data communicated from a means of detection. The data corresponds to the second flow of ions.

In another aspect, the invention relates to a system for measuring the mass of one or more reagent ions and one or more product ions. The reagent ions are generated by providing microwave or RF energy to a reagent vapor. The product ions are generated by interacting the reagent ions with a fluid sample in an electromagnetic field. The system includes an optical means for receiving a first flow of ions that includes the reagent ions and the product ions. The optical means also generates a second flow of ions directed towards an adjustment means. The system also includes the adjustment means for selectively controlling the second flow of ions to a mass spectrometer.

In another aspect, the invention relates to a method. The method involves introducing a sample gas. The method also involves supplying a reagent vapor to a plasma region and providing microwave or high-frequency RF energy to the reagent vapor in the plasma region to form one or more reagent ions. The method also involves interacting the one or more reagent ions with the sample gas to generate one or more product ions and directing the product ions and the reagent ions to a quadrupole or time-of-flight mass spectrometer module. The method involves determining by the mass spectrometer module a value for a peak intensity or mass of the product ions and the reagent ions.

In another aspect, the invention relates to a system. The system includes a microwave or high-frequency RF energy source to ionize particles of a reagent vapor with microwave or RF energy to form one or more reagent ions. The system includes a supply to facilitate analysis of a sample gas that includes one or more volatile organic compounds in at least a trace concentration. The system also includes a chamber with an inlet port that allows the sample gas to enter the chamber to interact with the reagent ions from the microwave or high-frequency RF energy source to form one or more product ions. The chamber has an electromagnetic field generated in the chamber. The system also includes a quadrupole or time-of-flight mass spectrometer module disposed relative to an exit orifice of the chamber to collect the product ions and reagent ions to facilitate a determination of a value for a peak intensity or mass of the product ions and reagent ions.

In yet another aspect, the invention relates to a mass spectrometry system including a means for introducing a sample gas including one or more volatile organic compounds in at least a trace concentration. The system includes a means for generating one or more reagent ions from a reagent vapor supply by providing the reagent vapor supply with microwave or high-frequency RF energy. The system includes a means for interacting the sample gas with the reagent ions to form one or more product ions. The system also includes a means for directing the product ions and the reagent ions to a mass spectrometer module for determining at least one of a peak intensity or mass of the product ions and the reagent ions or for identifying the volatile organic compounds in the sample gas.

Additional features relate to the above aspects. For example, the sample gas includes one or more volatile organic compounds in at least a trace concentration. The trace concentration can be between about one part-per-trillion and about one part-per-billion by volume. The trace concentration can be between about one part-per-billion and one part-per-million by volume.

The method can also involve coupling a gas sample inlet port to an enclosed space. The method can also involve positioning a gas sample inlet port in a non-enclosed space. The gas sample inlet port can be coupled to a container. In some embodiments, the gas sample inlet port is coupled to an exhaust of an automobile or an aircraft. The gas sample inlet port can be coupled to a head-space above a food or beverage product to, for example, determine the contents of the food or beverage product.

In some embodiments, the method involves positioning a gas sample inlet port in proximity to a human mouth to introduce exhaled breath in to the port. The method can involve positioning a gas sample inlet port in proximity to a solid sample material that is emitting a gas or vapor. In some embodiments, the gas sample inlet port is coupled to a supply of gas.

The quadrupole or time-of-flight mass spectrometer module can facilitate a determination of at least one of the peak intensity or mass of the volatile organic compounds in the gas sample, or the identity of the volatile organic compounds. Volatile organic compounds that can be measured, detected, and/or identified, including in trace concentrations, include dioxin-based compounds, furan-based compounds, chlorophenols, naphthalene, benzene, toluene, ethylbenzene, xylene, non-methane organic compounds, secondary organic aerosols, isobaric compounds, chemical warfare agents, battlefield gases, fire accelerants, VOC species emitted by bodily fluids, or through the action of fungal species (e.g., mycotoxins), or any combination of these. In some embodiments, the volatile organic compounds include anthropogenic or biogenic volatile organic compounds. In some embodiments, the sample gas includes inorganic gas or vapor species (e.g., hydrogen sulfide).

The details of one or more examples are set forth in the accompanying drawings and the description below. Further features, aspects, and advantages of the invention will become apparent from the description, the drawings, and the claims.

DETAILED DESCRIPTION

Figure 1:
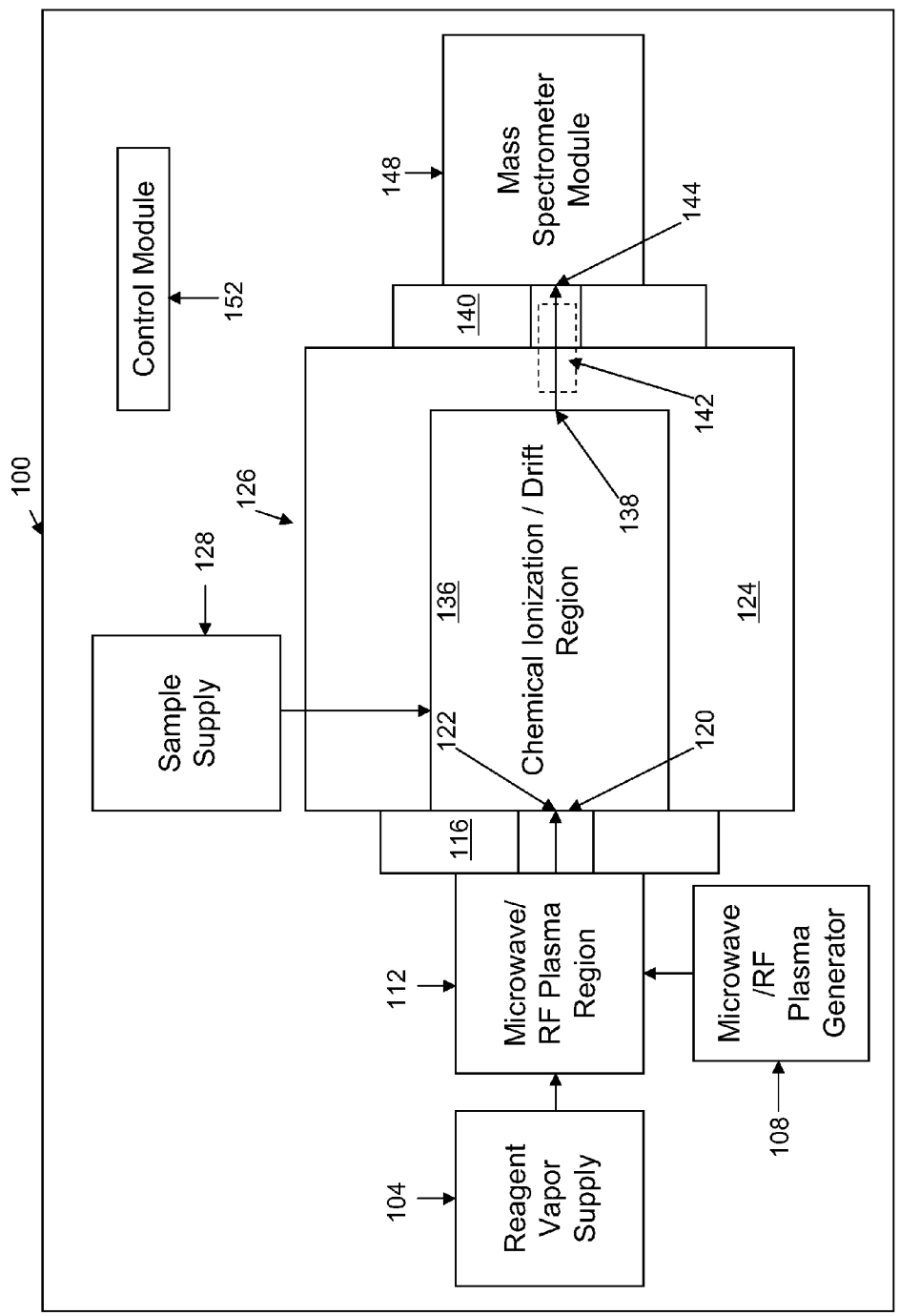
FIG. 1 is a plan view illustrating components of a system that embodies the invention.

FIG. 1 is a plan view illustrating components of a system 100 that embodies the invention. The system 100 includes a reagent vapor supply 104 and a plasma generator 108. The microwave/RF plasma generator 108 can generate a plasma using microwave energy (a microwave plasma) or high-frequency RF energy (an RF plasma). The RF energy can be supplied by a capacitively-coupled high-frequency RF energy source (not shown). A reagent vapor (not shown) from the reagent vapor supply 104 interacts with the plasma in the plasma region 112 to form the desired or particular reagent ion, which can be one or more of multiple different species, depending on the particular application for the system 100. In some embodiments, the plasma region 112 and the microwave/RF plasma generator 108 form portions of the same assembly (not shown) such that the reagent vapor interacts with the plasma within the assembly. In some embodiments, the plasma region 112 is disposed within a glass tube.

The plasma region 112 is in fluid communication with an electrically isolated orifice plate electrode 120 that is mounted within a flange 116. An insulator (not shown) is disposed between the flange 116 and the orifice plate electrode 120 to provide electric isolation therebetween. An electric potential is applied to the orifice plate electrode 120 to increase the potential of the plasma, thereby directing the one or more reagent ions through an aperture 122 defined by the flange 116 and the orifice plate electrode 120 and into the chemical ionization/drift region 136 within a drift outer chamber 124. The chemical ionization/drift region 136 is maintained at a lower potential than the orifice plate electrode 120. A sample supply 128 is in fluid communication with the chemical ionization/drift region 136 to provide a sample fluid (e.g., a sample gas) to the system 100. The sample gas flows into an inlet port (not shown) for passing through a surface (not shown) of the drift outer chamber 124 and into the chemical ionization/drift region 136. The inlet port is positioned downstream of the orifice plate electrode 120, which is centrally located within the flange 116, allowing the reagent ions to mix with components of the sample gas within the chemical ionization/drift region 136. Other configurations for introducing reagent ions and the sample gas into the chemical ionization/drift region 136 exist and are within the scope of the invention. For example, the inlet port can be coupled directly to the flange 116 to create a "shower-head" effect as the sample gas flows through fluid pathways (not shown) positioned radially about the aperture 122.

The drift assembly 126 includes a chemical ionization/drift region 136 and a pumped drift outer chamber 124. The pumped drift outer chamber 124 effectively houses the chemical ionization/drift region 136. The chemical ionization/drift region 136 can be defined by a series of electrodes and insulating plates (with intermediate o-ring seals (not shown)), each having a centrally disposed passage therethrough. The chemical ionization/drift region 136 is discussed in greater detail with respect to FIGS. 5 and 6. The chemical ionization/drift region 136 facilitates interactions (e.g., chemical reactions) between the sample and the reagent ions. The interactions between the sample and the reagent ions form one or more product ions. Typically, the reagent ions greatly outnumber components of the sample gas, and the reagent ions can be monitored in the product ion stream after the product ions are created. The chemical ionization/drift region 136 generally includes an electromagnetic field (not shown) to facilitate the interaction between the sample and the reagent ions as the sample and reagent ions mix within the chemical ionization/drift region 136. The electromagnetic field in the chemical ionization/drift region 136 also directs the reagent ions and the product ions towards an exit orifice 138.

Ions passing through the chemical ionization/drift region 136 through the exit orifice 138 are focused onto an exit orifice 144 defined by a flange 140. The exit orifice 144 allows ions to exit the drift outer chamber 124. The ions are focused onto the exit orifice 144 by a lens assembly 142. In some embodiments, the lens assembly 142 includes a focus aperture. Some embodiments employ a three-element Einzel lens for the lens assembly 142. The lens assembly 142 directs ions toward a mass spectrometer module 148, for example, according to specified flow parameters, such as flux, velocity or momentum of the ions. The lens assembly 142 can be used to optimize the number of ions that pass through the exit orifice 144. In some embodiments, the system 100 does not include a lens assembly.

The mass spectrometer module 148 determines the mass and quantity of the reagent ions and the product ions, for example, by collecting ions. The mass spectrometry module 148 produces and/or analyzes the resultant mass spectrum representative of the reagent and product ions that pass through the exit orifice 144. The mass spectrum associated with the product ions can be used to determine the existence, quantity, volume, concentration, or identity of constituents of the sample provided by the sample supply 128. Measurement of the reagent ions is used to calibrate and/or error-check the system 100. The mass spectrometer module 148 can be a quadrupole mass spectrometer or a time-of-flight mass spectrometer.

The system 100 also includes a control module 152. The control module 152 receives data about the operating conditions or parameters of the system 100. Based on the data, the control module 152 can determine or set input values or input operating parameters for the components of the system. For example, the control module 152 can receive data from the reagent vapor supply 104, the plasma generator 108, the plasma region 112, the orifice plate electrode 120, the chemical ionization/drift region 136, the lens assembly 142, the exit orifice electrode 144, or the mass spectrometer module 148. The control module 152 can, in response to the collected data, set input values for each of these components, for example, when the system 100 is initiated or in response to the data received regarding operational parameters.

In some embodiments, the control module 152 updates the input values for the operating parameters automatically in response to data received about operational parameters. For example, if the operational parameters relating to the pressure or electromagnetic field within the chemical ionization/drift region 136 deviate from the specified or desired values for those parameters, the control module 152 can adjust the sample supply 128 that sets the pressure in the chemical ionization/drift region 136 or the electrodes (not shown) that create the electromagnetic field until the parameters correspond to the input or correct values for those parameters. Other operational parameters include velocity or energy of reagent ions or product ions in the system 100, a flow rate of the fluid sample into the chemical ionization/drift region 136, a flow rate of reagent ions into the chemical ionization/drift region 136, a composition of the sample, relative concentration of the sample and reagent ions, or relative concentration of reagent ions and product ions. In some embodiments, the control module 152 monitors multiple operational parameters of the system 100.

In some embodiments, the control module 152 uses a plasma metrology process for receiving and/or updating parameters of the system 100. The plasma metrology process can monitor, for example, light emission spectra from the plasma region 112. Based on light emission spectra, the control module 152 determines the value of operating parameters within the plasma region 112 (e.g., "plasma parameters), for example, the intensity of a particular emission wavelength, and if the parameter deviates from a specified or desired value, the control module 152 can adjust the plasma parameters until these parameters correspond to optimum values for those parameters. If the control module 152 is unable to achieve optimum conditions or parameters, then a fault condition may be detected and/or registered.

In some embodiments, a mass filter (not shown) can be positioned between the microwave/RF plasma region 112 and the chemical ionization/drift region 136. The mass filter can be used to selectively allow reagent ions to pass into the chemical ionization/drift region 136. In some embodiments, the mass filter is a quadrupole mass filter.

The system 100 includes one or more ports (not shown) coupled to one or more pumps (not shown) for establishing values for pressures throughout the system 100. For example, pressure values within the microwave/RF plasma region 112, the chemical ionization/drift region 136, the pumped drift outer chamber 124, and the mass spectrometer module 148 are maintained by one or more pumps.

Figure 2:
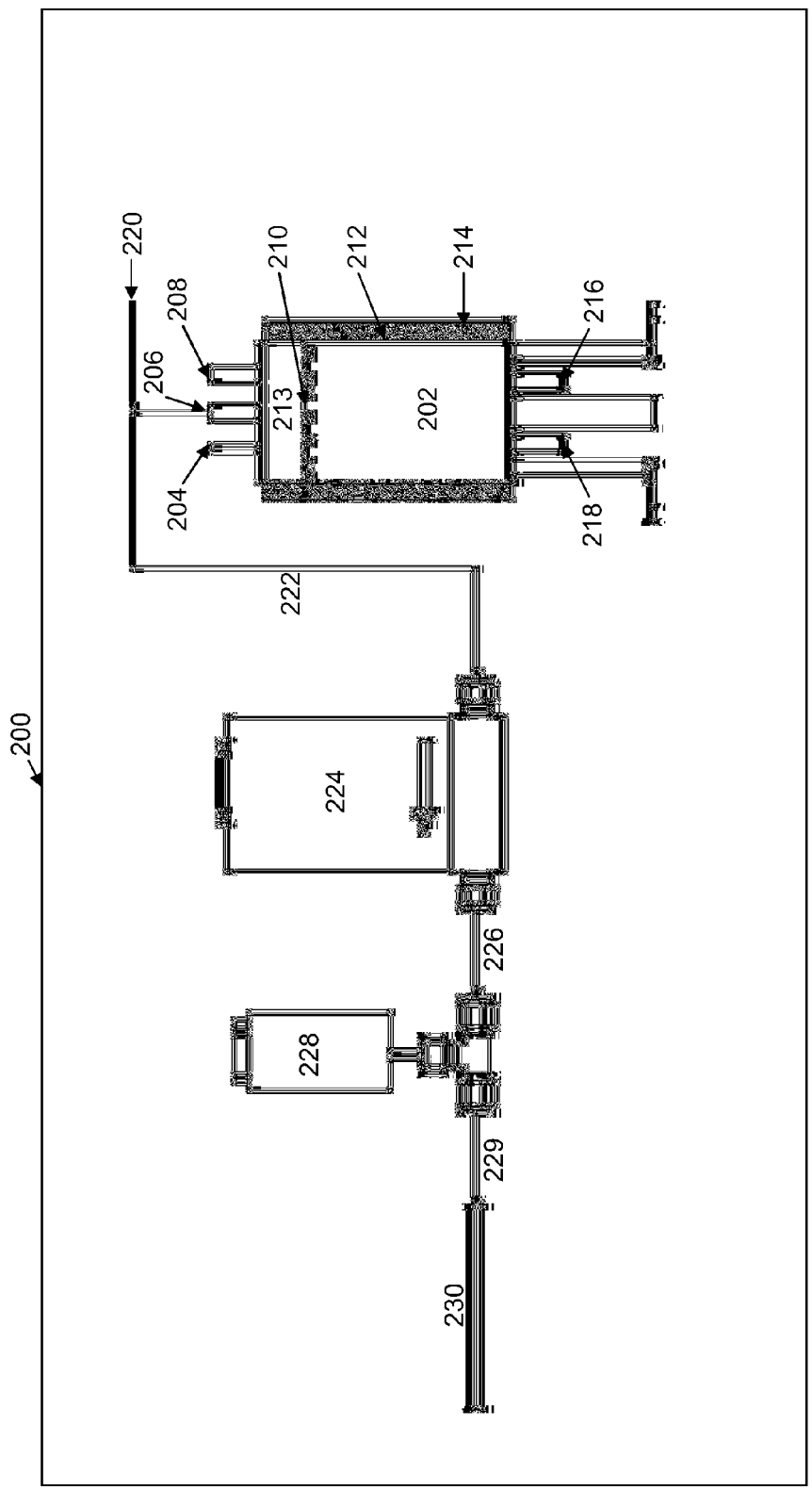
FIG. 2 is a cross sectional view of a reagent vapor supply assembly for a mass spectrometry system.

FIG. 2 is a cross sectional view of a reagent vapor supply assembly 200 for a mass spectrometry system (e.g., the system 100 of FIG. 1). The assembly 200 is configured to provide a consistent or stable flux or flow of vapor to an energy source, for example, the plasma generator 108 of FIG. 1. The vapor provided by the assembly 200 includes one or more reagent molecules that are ionizable by a microwave or RF plasma and is sometimes referred to as reagent vapor. The assembly 200 includes a reservoir 202 for housing a fluid supply. The reservoir 202 can be constructed from stainless steel or other suitable metals.

In some embodiments, the reservoir 202 houses water or pure water to create water vapor. As illustrated, the reservoir 202 includes five ports. The port 204 is connectable to a tube or channel for the introduction of a fluid to the reservoir (e.g., for topping off the water or fluid supply). The port 206 is connectable to a tube or channel for delivering or passing the reagent vapor to the mass spectrometry system. The port 208 is connectable to a tube or channel for obtaining measurements about the fluid within the reservoir 202. For example, the port 208 can be coupled to a capacitor manometer gauge for determining the headspace pressure within the reservoir 208. In some embodiments, the port 208 is not used. The port 216 is connectable to a tube or channel for measuring the quantity of fluid in the reservoir 202 (e.g., for connection to a water level indicator). The port 218 is connectable to a tube or channel for draining or emptying the reservoir 202 of fluid. Each of the ports 208 and 216 are optional, and in some embodiments are not included in the system 200 or are not used for mass spectrometry operations. In some embodiments, each of the ports 204, 206, 208, 216, and 218 are connectable to tubes of 0.25 inch diameter (about 0.635 centimeter). Other size tubes or channels can be connected to the ports, and the tubes or channels need not be of the same size.

In some embodiments, the reservoir 202 is heated to a specific elevated temperature using a heater jacket 214 that envelops the reservoir 202. In some embodiments, the control module 152 of FIG. 1 is coupled to a thermocouple 212. The temperature of the reservoir 202 (and the fluid therein) can be an operational parameter maintained, regulated, and adjusted by the control module 152 in response to operation of the mass spectrometry system. This control enables a user to maintain the vapor pressure in the headspace 213 above the liquid surface 210 at a specified or desired value.

The assembly 200 also includes tubing 222 that is coupled in fluid communication to a mass flow controller 224. The mass flow controller 224 can determine the quantity of reagent vapor that flows through tubing 226 and into the plasma region 230, where production of reagent ions occurs by application of microwave or RF energy to the reagent vapor. In some embodiments, the mass flow controller 224 can be a heated mass flow controller with separate electronics which are located remotely from the assembly 200 (not shown).

Other types of flow controller can be used in conjunction with or instead of the mass flow controller 224. As illustrated, the assembly 200 includes a gauge or monitor 228 for indicating the value of the pressure within the plasma region 230. The gauge can be a capacitance manometer gauge. In some embodiments, the control module 152 of FIG. 1 is coupled to the gauge or monitor 228, and the pressure within the plasma region 230 is an operational parameter maintained, regulated, and adjusted by the control module 152. In some embodiments, the gauge or monitor 228 is not included in the assembly 200.

In some embodiments, the tubing 222 and the tube 226 are made of stainless steel and define an outside diameter of about 0.25 inches (about 0.635 centimetres). The tube 229 electrically isolates the main body of the assembly 200 from the plasma region 230. In some embodiments, the tube 229 is made of polytetrafluoroethylene ("PTFE") and defines an outside diameter of about 0.25 inches (about 0.635 centimetres). The pressure within the plasma reaction region 230 can be about 1-5 torr (about 100-700 Pascal) during mass spectrometry operations. The pressure within the assembly 200 is maintained by a pump (not shown) that is external to the assembly 200. For example, a pump coupled to the drift outer-chamber 124 (and in-turn, to the chemical ionization/drift region 136) of FIG. 1, can be used to establish the pressure with the assembly 200 via fluid communication with the assembly 200. The chemical ionization region 136 of FIG. 1 can be coupled in fluid communication with the assembly 200 via the aperture 122 and the plasma region/tube 112.

In some embodiments, a port 220 is used to mix the reagent vapor with another gas to improve reagent ion production during application of microwave or RF energy. For example, the mixing gas can be argon, nitrogen or an argon/nitrogen mixture. In some embodiments, a gas or gas mixture (e.g., NO or $O_2$) to be used in reagent ion generation is introduced via port 220, and the reservoir 202 is fluidly isolated from the tubing 222 by a valve (not shown).

Figure 3:
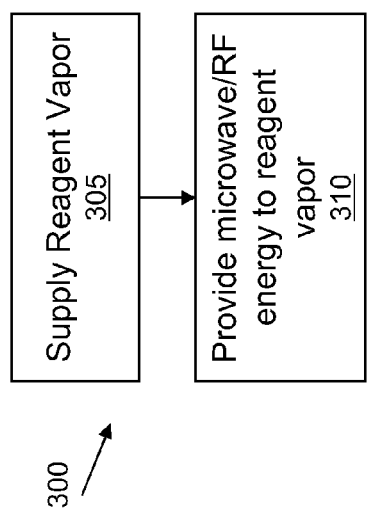
FIG. 3 is a flow chart of a method for generating reagent ions.

FIG. 3 is a flow chart 300 of a method for generating reagent ions. In step 305, a reagent vapor is supplied. For example, a reagent vapor can be supplied according to the system 200 illustrated in FIG. 2, such that a relatively consistent or stable flow of reagent vapor is supplied. The reagent vapor can be pure water vapor or water vapor mixed with a plasma mixing gas, such as argon or nitrogen or a mixture thereof. In some embodiments, the reagent vapor includes reagent species such as nitrous oxide (NO) or diatomic oxygen ($O_2$).

In step 310, energy is provided to the reagent vapor. In some embodiments, the energy is microwave radiation, which is used to form an ionized microwave plasma. In some embodiments, the energy is high-frequency RF power, which is used to form an RF plasma, for example, of the type produced by a capacitively-coupled RF energy source. Microwave energy generally refers to energy (e.g., radiative energy) produced by electromagnetic waves having frequency values greater than about 800 MHz and less than about 300 GHz. High-frequency RF energy generally refers to energy (e.g., radiative energy) produced by electromagnetic waves having frequency values greater than about 400 kHz and less than about 800 MHz. In particular, RF energy can be provided within frequency values specified by the Industrial, Scientific, and Medical ("ISM") radio center band frequencies.

The energy applied in step 310 energizes or excites molecules in the flux of reagent vapor to generate reagent ions. The molecules in the reagent vapor stream are ionized by the plasma. For example, when water vapor is used as the reagent vapor, hydronium ions are produced through multi-step reactions:

$e^- + H_2O \rightarrow H_2O^+ + 2e^-$  Reaction 1

$H_2O^+ + H_2O \rightarrow H_3O^+ + OH$  Reaction 2

Reaction 1 involves an interaction between a free electron ($e^-$) from the ionized plasma interacting with a water molecule ($H_2O$) to form a positively-charged, ionized water molecule and a second free electron. In Reaction 2, the positively-charged water molecule interacts with a neutral water molecule to form a hydronium ion ($H_3O^+$) and a hydroxyl radical. Hydronium ions can be reagent ions for subsequent interactions with constituents of a fluid sample.

Both microwave and high frequency RF plasmas are desirable because they offer an efficient means of generating a rich source of the ions and electrons which are required for the production of reagent ion species—e.g. hydronium ions. Furthermore, microwave and high frequency RF plasmas are relatively clean, with little or no internal sputtering often associated with hollow cathode/glow discharge plasma sources, where electrodes are in direct contact with the plasma. The "electrode-less" nature of microwave and high frequency RF plasma sources means that the impact of instability and drift associated with electrode erosion is reduced. Moreover, microwave and high frequency RF plasma sources are capable of providing relatively constant, high levels of reagent ions.

In some embodiments, the method of FIG. 3 includes an additional step (not shown) involving measuring the pressure of the microwave or high frequency RF plasma. The value of the plasma pressure can be a control parameter for a mass spectrometry system (e.g., controllable by the control module 152 of FIG. 1). The plasma pressure can also be used to determine the appropriate supply of reagent vapor (e.g., from the assembly 200).

Figure 4:
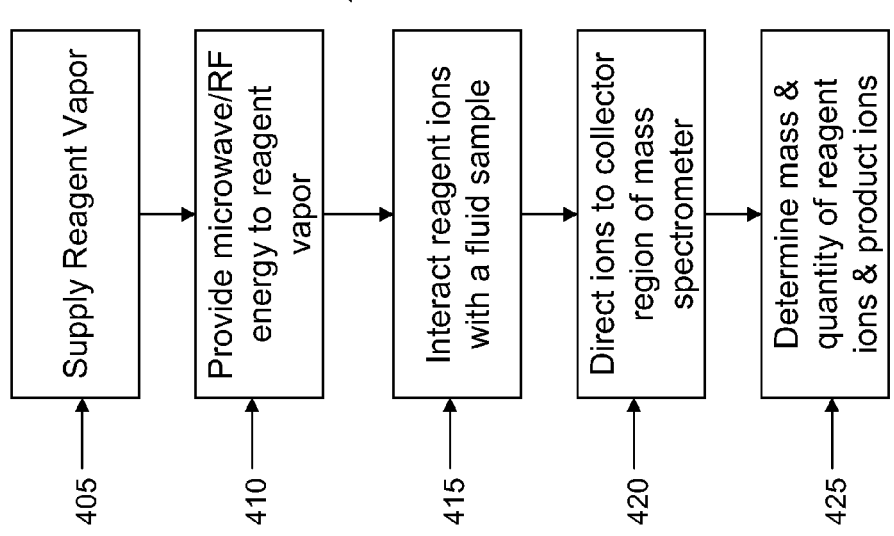
FIG. 4 is a flow chart depicting a mass spectrometry method that embodies the invention.

FIG. 4 is a flow chart depicting a mass spectrometry method 400 that embodies the invention. Step 405 involves supplying a reagent vapor, and step 410 involves providing microwave or RF energy to the reagent vapor to generate reagent ions, for example as discussed above with respect to FIG. 3. The reagent ions are then directed to a chemical ionization/drift region by a combination of fluid flow phenomenon resulting from the pressure drop between the plasma reaction region and the chemical ionization/drift region and the influence of an electromagnetic field gradient from an ion extraction orifice or electrodes within the chemical ionization/drift region.

In step 415, a fluid sample (e.g., a gas containing molecules of one or more volatile organic compounds) interacts with the reagent ions. Mixing the fluid sample and the reagent ions results in interactions between the fluid sample and the reagent ions. For example, the fluid sample can be supplied to the flow of reagent ions via an inlet line, which passes through the drift outer chamber and into the chemical ionization/drift region. A pressure drop between the sample supply and the chemical ionization/drift region can facilitate fluid flow carrying the fluid sample into the chemical ionization/drift region. The chemical ionization/drift region includes an electromagnetic field that facilitates movement of the reagent ions within the region and facilitates collisions between reagent ions and constituents of the fluid sample. Collisions between reagent ions and constituents of the fluid sample result in a chemical reaction that ionizes particles of the fluid sample. An example of a chemical reaction involving a hydronium ion and a sample species, R, of a constituent molecule with a proton affinity greater than that of water is shown below:

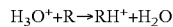

$H_3O^+ + R \rightarrow RH^+ + H_2O$    Reaction 3

Chemical reactions involving hydronium ions and species R are low-energy and/or soft ionization interactions. The integrity of the sample molecules is not significantly altered and molecular fragmentation of the sample is reduced or minimized, for example, when compared with higher energy ionization processes, such as electron impact ionization. Moreover, species in the sample with a proton affinity less than that of water are not ionized by collisions with hydronium atoms and, therefore, are not detected during mass spectrometry. Examples of such species include common constituents of air including diatomic nitrogen, diatomic oxygen, argon, carbon dioxide, and methane. In general, these constituents of air produce high intensity spectral peaks in an acquired mass spectrum based on the large proportion of the constituents of air in the sample relative to constituents present in the sample at trace quantities. High-intensity spectral peaks can obscure nearby low-intensity peaks or can increase difficulty in distinguishing low-intensity peaks from high-intensity peaks. Therefore, the selective nature of this chemical ionization technique can enhance the ability to distinguish the spectral peaks due to low intensity/trace level species in the sample.

In step 420, reagent ions and product ions are directed out of the chemical ionization/drift region, through a lens or exit orifice assembly and towards the collector region of a mass spectrometer. In some embodiments, the reagent ions and product ions are directed out of the chemical ionization/drift region by an electromagnetic field established in the chemical ionization/drift region. The reagent and product ions can pass out of an orifice at the end of the chemical ionization/drift region, through a lens assembly, through an ion extraction orifice, and into the mass spectrometer module. The lens assembly can feature a focus aperture, or can feature a three-element Einzel lens. In some embodiments, the ion extraction orifice is disposed within a flange. Electrical potentials can be applied to the lens assembly and ion extraction orifice such that an electric field is generated to direct the reagent and product ions through the orifice. In general, the mass spectrometer module is operated at a relatively high-vacuum to ensure that molecular flow conditions prevail for the effective operation of the mass spectrometer and its component parts.

The mass spectrometer module can include a quadrupole mass spectrometer or a time of flight mass spectrometer. For either type of mass spectrometer, the reagent and product ions are directed to a collector region of the mass spectrometer. The ions collide with a detector in the collector region, and the resulting current is amplified in the mass spectrometer (e.g. using a combination of an electron multiplier with a preamplifier). Based on input from the collector, the mass spectrometer accumulates data about the reagent and product ions and generates a signal spectrum indicative of the mass values (or mass-to-charge ratio) and quantity of the collected ions.

Step 425 involves determining the mass and quantity of reagent ions and product ions, for example, based on the mass spectrum generated. Well-resolved peaks in the mass spectrum can be used to determine the exact mass or mass-to-charge ratio of both reagent and product ions. The specific location of these peaks also facilitates identification of components of the fluid sample by comparison of the mass values determined from the spectral or signal peaks with molecules or ions of known mass. In some embodiments, an analysis module can be used to display the signal spectrum and/or to determine the existence and location of peaks in the spectrum.

Figure 5:
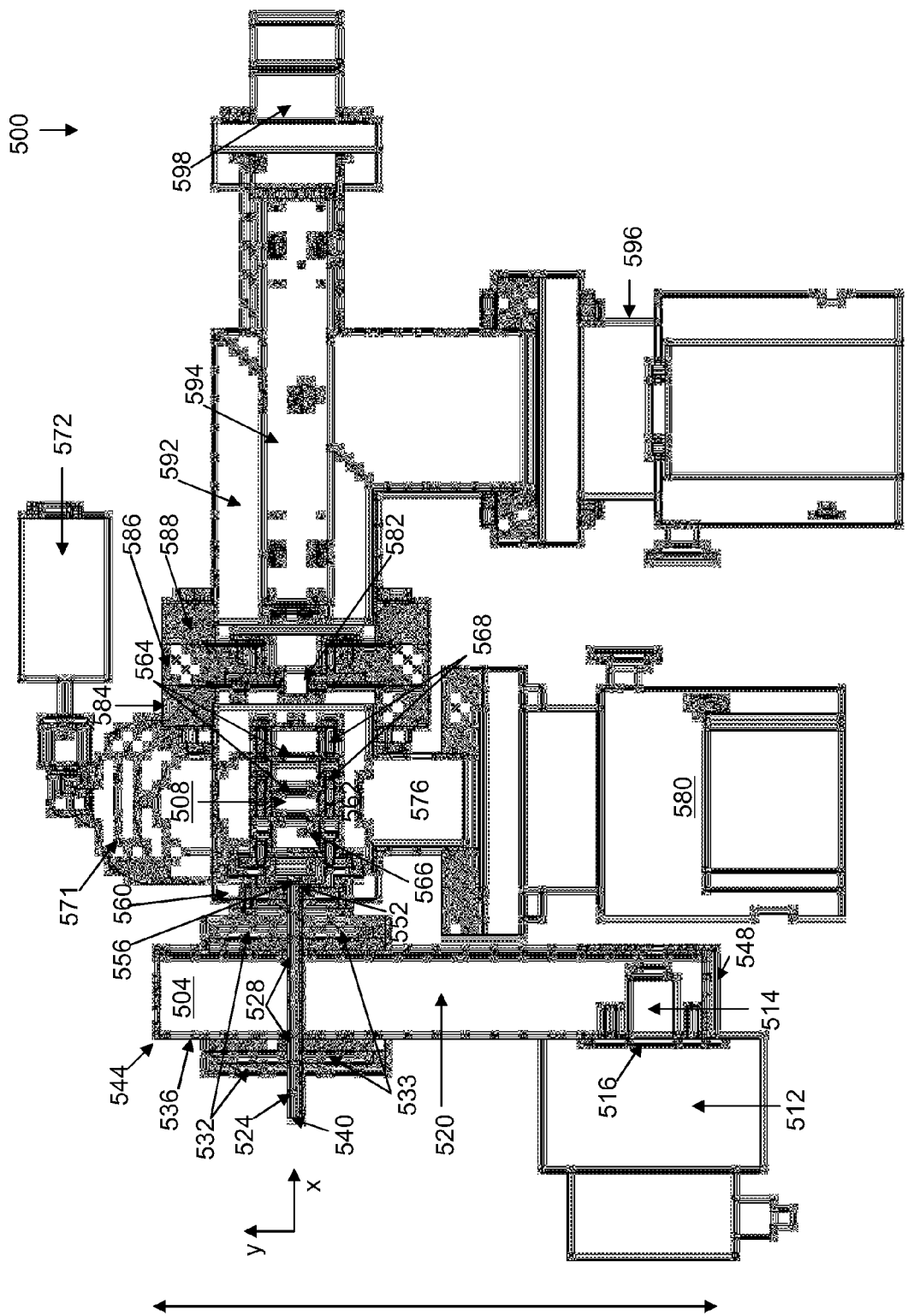
FIG. 5 is a cross-sectional view of a quadrupole mass spectrometry system that embodies the invention.

FIG. 5 is a cross-sectional view of a quadrupole mass spectrometry system 500 that embodies the invention. The system 500 includes a reagent ion source 504 coupled to a chemical ionization/drift region 508. The reagent ion source 504 in the system 500 is based on a microwave energy source that includes a magnetron 512 with a stub aerial 514 disposed through an aperture 516 of a resonant cavity 520. In some embodiments, the reagent ion source energy source 504 can be based on a high-frequency energy source, such as an RF energy source. The reagent ion source 504 also includes a tube 524 passing through the resonant cavity 520 via apertures 528. The tube 524 also passes through two microwave chokes 532 that are disposed on an exterior surface 536 of the resonant cavity 520. The microwave chokes 532 reduce an amount of microwave energy that escapes the resonant cavity 520 or the tube 524 and reduces the microwave energy extending to other components of the system 500. The tube 524 can be made from silica or a silica material, such as quartz. In some embodiments, the tube 524 can be made of sapphire. An end 540 of the tube 524 can be coupled to a corresponding end (not shown) of a reagent vapor supply (not shown) for providing a reagent vapor to the reagent ion source 504. For example, the end 532 can be coupled to the tube 229 of the reagent vapor supply system 200 illustrated in FIG. 2.

In some embodiments, the tube 524 has an outside diameter of about 6 millimeters. The resonant cavity 520 defines a length l along the y-axis. The length l corresponds to or is about equal to one full wavelength λ of the lowest-order resonant mode of the resonant cavity 520. The tube 524 is positioned a distance of about ¼λ along the y-axis from the top 544 of the resonant cavity 520. More specifically, the tube 524 is positioned at an anti-node of the resonant cavity 520 to maximize the resonant energy that is transferred from the resonant cavity 520 to the tube 524.

In some embodiments, the magnetron 512 is a 900-Watt magnetron with stub aerial 514 that provides microwave power to the resonant cavity 520. The power is radiatively distributed by electromagnetic waves having frequency values in the microwave spectrum in the resonant cavity 520 and is transferred to the tube 524. As a result of the resonant energy within the cavity 520 interacting with the reagent vapor inside the tube 524, a plasma is generated inside the tube 524. The reagent vapor enters the tube 524 via the end 540 coupled to the reagent vapor supply. Owing to a pressure drop between the tube 524 and the chemical ionization/drift chamber 508, the reagent vapor supply provides or directs a flow of reagent vapor into the tube 524, for example, along the x-axis. The continual flow of reagent vapor ensures that a microwave plasma is sustained inside the tube 524 to generate one or more reagent ions, for example, as discussed above.

In some embodiments, the resonant cavity 520 is constructed from a silver-plated aluminum extrusion with enclosed ends (e.g., the top 544 and bottom 548 of the cavity 520). In some embodiments, the microwave chokes 532 are cylindrical in shape with a centerline (not shown) parallel, co-axial, or collinear with the x-axis. The microwave chokes 532 can be made from either stainless steel or aluminum. In some embodiments, a channel 533 is disposed within one or both of the microwave chokes 532. The length of the channel 533 can be approximately ¼ l along the y-axis.

A second end 552 of the tube 524 terminates at the face 557 (see FIG. 6) of an orifice plate 556 retained within a flange 560 and attached to the chemical ionization/drift region 508. Reagent ions pass from the tube 524 through the orifice plate 556 and into the chemical ionization/drift region 508. The chemical ionization/drift region 508 is defined in part by annular electrodes 564 disposed in a spaced relationship along the x-axis through the center of the drift outer chamber 562. An electric potential is applied to each of the electrodes 564 to generate an electromagnetic field. In some embodiments, the electromagnetic field has a linear field gradient directed along the x-axis. The value of the positive electric potential applied to each electrode decreases along the positive direction of the x-axis to generate the axially directed linear field gradient. A nonlinear field gradient can also be used. The electrodes 564 are electrically isolated from each other by annular insulative components 568 disposed therebetween. The electric field facilitates interaction between the reagent ions from the reagent ion source 504 (e.g., the tube 524) and the sample introduced at the chemical ionization/drift chamber port 566.

The drift outer chamber 562 also includes a pumping port 576 coupled to a pumping system 580. The drift outer chamber 562 also includes an electrical feedthrough port (not shown) and a port 571 with tube connectors (not shown) for the sample introduction line (not shown) and for fluid communication with a total pressure gauge 572 and a second gauge (not shown). In some embodiments, the pumping system 580 includes a turbomolecular pump with a diaphragm backing pump (not shown). The pumping system 580 establishes the required pressures within the drift outer-chamber 562 and chemical ionization/drift region 508. The pressure within the drift chamber 508 can be monitored by the total pressure gauge 572 and the pressure in the drift outer chamber 562 can be monitored by the second gauge (not shown). The data provided by these gauges can be supplied as inputs to a control module (not shown), for example, for system diagnostic processes.

The chemical ionization/drift region 508 and the drift outer chamber 562 includes a flange 584 that is coupled, through a double sided flange 586, to a corresponding flange 588 of the mass spectrometer 592. The mass spectrometer 592 depicted in the system 500 is a quadrupole mass spectrometer. The mass spectrometer 592 includes a spectrometer probe 594 and is coupled in fluid communication with a pumping system 596. The pumping system 596 establishes the pressure inside the mass spectrometer 592, for example, to facilitate measurement of the mass of the reagent ions and product ions and to reduce the negative effects on this measurement of the mass of ions resulting from interactions with ambient components in the mass spectrometer.

Ions passing from the chemical ionization/drift region 508 to the mass spectrometer 592 are directed to the mass spectrometer probe 594 by the ion extraction electrode 582. In some embodiments, an ion optical assembly (not shown) can be used in conjunction with the ion extraction electrode 582 to increase the number of reagent ions and product ions passed to the mass spectrometer 592. For example, a focus aperture or a three-element Einzel lens can be used. The spectrometer probe 594 can be an electrically-biased quadrupole mass analyzer or mass filter. A quadrupole mass analyzer includes four parallel metal rods positioned, for example, as vertices of a square and parallel to the x-axis. Opposing pairs of rods are electrically coupled to create two electrically coupled dipoles. A first RF energy or voltage with a positive DC voltage component can be applied to the rods of the first dipole, and a second RF energy or voltage with a negative DC voltage component can be applied to the rods of the second dipole. Ions which are on a stable trajectory through the mass filter pass between the rods in a direction that is generally parallel to the rods (e.g., parallel to the center axis of the square).

The RF and/or DC energy applied to the spectrometer probe 594 generates a mass-selective oscillating field. A mass-selective field results in an ion trajectory of a specified geometry, such as an oscillating geometry with a direction which is generally along the x-axis. The trajectory is specified such that ions having a value of a mass-to-charge ratio within a specified range can substantially follow the trajectory to the detector 598 while ions out of the specified range do not follow the trajectory to the detector 598. Non-selected ions collide with the rods and are not collected by the detector 598. In some embodiments, the mass-selective field varies according to the values of the energies applied to the quadrupole rods, e.g., as electric potential, DC energy or RF energy. A bandwidth of mass values can be selected by a particular field strength or flux. In addition, the spectrometer probe 594 can scan for mass ranges by varying the mass-selective field.

In some embodiments, the spectrometer probe 594 includes a linear, co-axial series of three quadrupoles called a triple-filter quadrupole mass analyzer. In such embodiments, the first and third elements of the triple-filter are relatively short (e.g., approximately 1-inch or 2.54 centimeters) "RF-only" filters, which carry the RF voltages element transmitted to them by the second or main filter. These "RF-only" pre- and post filters function as ion lenses and focus ions into and out of the mass filter assembly. The purpose of using pre- and post filters in this way is to improve the transmission of ions through the filter assembly, particularly those of a higher mass (e.g., more than about 80 atomic mass units) by increasing the number of ions transmitted. Pre- and post-filters also improve the mass resolution and abundance sensitivity performance of the filter. Ions successfully passing through the triple-filter assembly are collected by the detector 598. In some embodiments, the detector 598 is an electron multiplier detector. An electron multiplier detector amplifies the electric signal generated by ion collisions with the entrance or front face of the detector (not shown).

Figure 6:
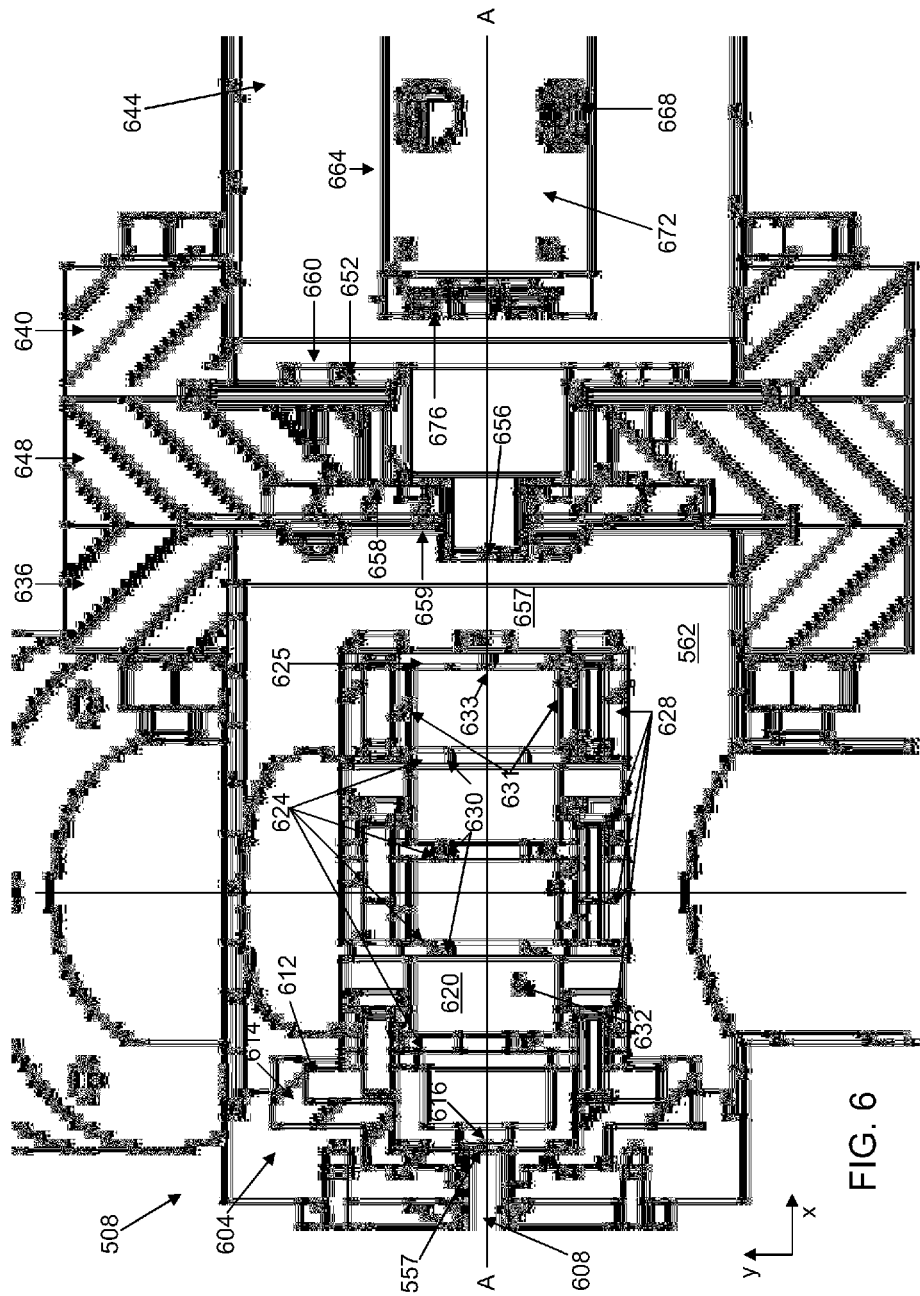
FIG. 6 is an enlarged view of the drift chamber assembly depicted in FIG. 5.

FIG. 6 is an enlarged view of the chemical ionization/drift region 508 depicted in FIG. 5. The chemical ionization/drift region 508 includes a chemical ionization/drift chamber 620 that is mountable on an ion extraction electrode 612 defining an extraction orifice 616. Reagent ions pass through the extraction orifice 616 when the reagent ions move from the plasma region 608 into the chemical ionization/drift region 508. The ion extraction electrode 612 can be coupled in fluid communication with an energy source (not shown). Ions pass through the extraction orifice 616 under the influence of an electromagnetic field generated by an electric potential applied to the extraction electrode 612. The extraction electrode 612 is coupled to a flange 604 by one or more screws (not shown) having ceramic inserts or inserts made of another insulative material. These screws and inserts pass through an insulating (e.g., ceramic or PEEK) collar 614 to further electrically isolate the extraction electrode 612 from the flange 604. In some embodiments, the value of the applied electric potential on the extraction electrode 612 affects the average energy of reagent ions as they proceed along the centerline A, which is substantially parallel to the x-axis, into the chemical ionization/drift chamber 620 of the chemical ionization/drift region 508. In addition, the size and/or geometry of the extraction orifice 616 determines an amount of flow of reagent ions into the chemical ionization/drift chamber 620.

Ions pass through the extraction orifice 616 in the extraction electrode 612 and into the into the chemical ionization/drift chamber 620 substantially along the centerline A (e.g., axially or parallel to the x-axis). An electromagnetic field is generated in the drift region 620 by an electric potential applied to each of one or more plate electrodes 624 and the drift end-plate electrode 625 (also referred to as an electrode stack). The electrodes can be made from a metallic or other conductive material. In some embodiments, the plate electrodes 624 and drift end-plate electrode 625 each have an annular shape with a central orifices 630 and 633 aligned with the centerline A. The central orifice 630 of each plate electrode can be approximately 10 millimeters in diameter. The central orifice 633 of the drift end-plate electrode can be approximately 1-2 millimeters in diameter. Other diameters and geometries (e.g., non-circular) are within the scope of the invention. The plate electrodes 624 and drift end-plate electrode 625 are physically separated and electrically isolated by one or more insulating collars 628. In some embodiments, the insulating collars 628 have an annular shape with a central orifice 631 aligned with the centerline A. The diameter of the central orifice 631 in the insulating collars 628 can be approximately 20 millimeters. Other diameters and geometries are within the scope of the invention. Suitable materials for the insulating collars 628 include polymer materials such as collars made from PEEK™, sold by Victrex plc of Lancashire, England or a static dissipative plastic such as SEMITRON®, sold by Quadrant Engineering Plastic Products of Reading, Pa. O-rings (not shown) are located within annular grooves on either side of each of the insulating collars 628. The o-rings facilitate a gas-tight seal at the interface between an insulating collar and a plate electrode 624 or the drift end-plate electrode 625. In some embodiments, these o-rings can be made of a VITON® fluoroelastomer sold by Du Pont Performance Elastomers of Wilmington, Del.

The extraction electrode 612, the plate electrodes 624, and the drift end-plate electrode 625 cooperate to generate the electromagnetic field within the chemical ionization/drift chamber 620. In some embodiments, the electromagnetic field has a linear field gradient along the x-axis. The electromagnetic field gradient can also be non-linear, for example, based on differences between the electric potential applied to the extraction electrode 612, each of the plate electrodes 624, and the drift end-plate electrode 625. The electromagnetic field directs reagent ions and facilitates an interaction between the reagent ions and constituents of the sample fluid.

In some embodiments, a decreasing electric potential is applied to each of the plate electrodes 624 and drift end-plate electrode 625 along the centerline A in an increasing direction along the x-axis to facilitate flow of the reagent ions and product ions within the chemical ionization/drift chamber 620. Sample gas is supplied to the chemical ionization/drift chamber 620 from a sample supply (not shown), for example, as discussed in FIG. 1 via a port in the drift outer chamber (e.g., port 571 of FIG. 5) and then via a port 632 in the side of an insulating collar 628. A similar port in the side of another insulating collar 628 can be in fluid communication with the gauge 572 on port 571 of FIG. 5 to facilitate the measurement of pressure within the chemical ionization/drift chamber 620. In some embodiments, the sample supply consists of a mass flow controller which is used to control the flow of fluid sample entering the chemical ionization/drift chamber 620. The sample gas evolves along the centerline A in an increasing direction along the x-axis and interacts with reagent ions. The plate electrodes 624 and drift end-plate electrode 625 are secured to the extraction electrode 612, which supports the plate electrodes 624 and drift end-plate electrode 625 within the chemical ionization/drift chamber 620.

In some embodiments, a control module (not shown) is coupled to the ion extraction electrode 612, each of the plate electrodes 624, and the drift end-plate electrode 625 for providing an electric potential to each of the electrodes 612, 624 & 625. The control module also monitors other parameters inside the chemical ionization/drift chamber 620, such as the field gradient, pressure, or detected ion intensity. When a value for a particular monitored parameter deviates from a predetermined threshold, the control module can reset or adjust the value for the electric potential applied to the ion extraction electrode 612, each of the plate electrodes 624, and the drift end-plate electrode 625.

In some embodiments, the control module automatically changes the potential of the ion extraction electrode 612, each of the plate electrodes 624, and the drift end-plate electrode 625 in response to changes in parameters of the chemical ionization/drift chamber 620, via a feedback loop. For example, the control module can establish as an initial condition or mode an electric field gradient and pressure which defines the optimum e/n (e.g., charge density) setting for a given sample monitoring requirement. In some embodiments, the control module can monitor the parameters of the chemical ionization/drift chamber 620 and maintain optimum e/n levels through the real-time adjustment of electrical field gradient and/or pressure. In some embodiments, the control module can make changes to the chemical ionization/drift chamber 620 field gradient and/or pressure levels, based on a user induced adjustment of e/n level—e.g. when using different e/n levels to discriminate between two isobaric compounds. In some embodiments, the electric field gradient established by the ion extraction electrode 612, each of the plate electrodes 624, and the drift end-plate electrode 625 is linear along the x-axis (or the centerline A). In some embodiments, the electric field gradient is non-linear. Another parameter which can be monitored by the control module and associated with electric field, pressure and e/n levels within the chemical ionization/drift chamber 620 is the ratio of product ions to reagent ions.

The drift outer chamber 562 incorporates a fixed flange 636 that is secured to a corresponding flange 640 of the mass spectrometer 644 with a double-sided flange 648 disposed therebetween. An ion extraction electrode 652 defining an extraction orifice 656 is secured to the flange 648, for example, by one or more insulated screws 660. An insulating collar 658 (e.g., made of ceramic) electrically isolates the ion extraction electrode 652 from the double-sided flange 648. A metallic plate 659 shields the insulating collar 658 and reduces the build-up of surface charge, which could interfere with ion optics in the region 657 between the chemical ionization/drift chamber 620 and the mass spectrometer 644. An electric potential is applied to the ion extraction electrode 652 to create a field that directs reagent ions and product ions from the chemical ionization/drift chamber 620 to the mass spectrometer 644. The mass spectrometer 644 includes a spectrometer probe 664 having one or more holes 668 to facilitate vacuum pumping and/or evacuating the mass spectrometer 644 and the spectrometer probe 664. The spectrometer probe 664 is substantially aligned with the centerline A, and ions can enter the spectrometer probe 664 along the centerline A through the focus electrode 676. The spectrometer probe 664 is coupled to an analysis module that generates and/or displays a mass spectrum based on reagent and product ions collected by a detector (not shown) coupled to the spectrometer probe 664. In some embodiments, additional ion optics (not shown) are used in the region 657 between the chemical ionization/drift chamber 620 and the mass spectrometer 644, for example, to optimize the levels of reagent and product ions reaching the mass spectrometer 644. Ion optics may take the form of a focus aperture or a three-element Einzel lens.

Figure 7:
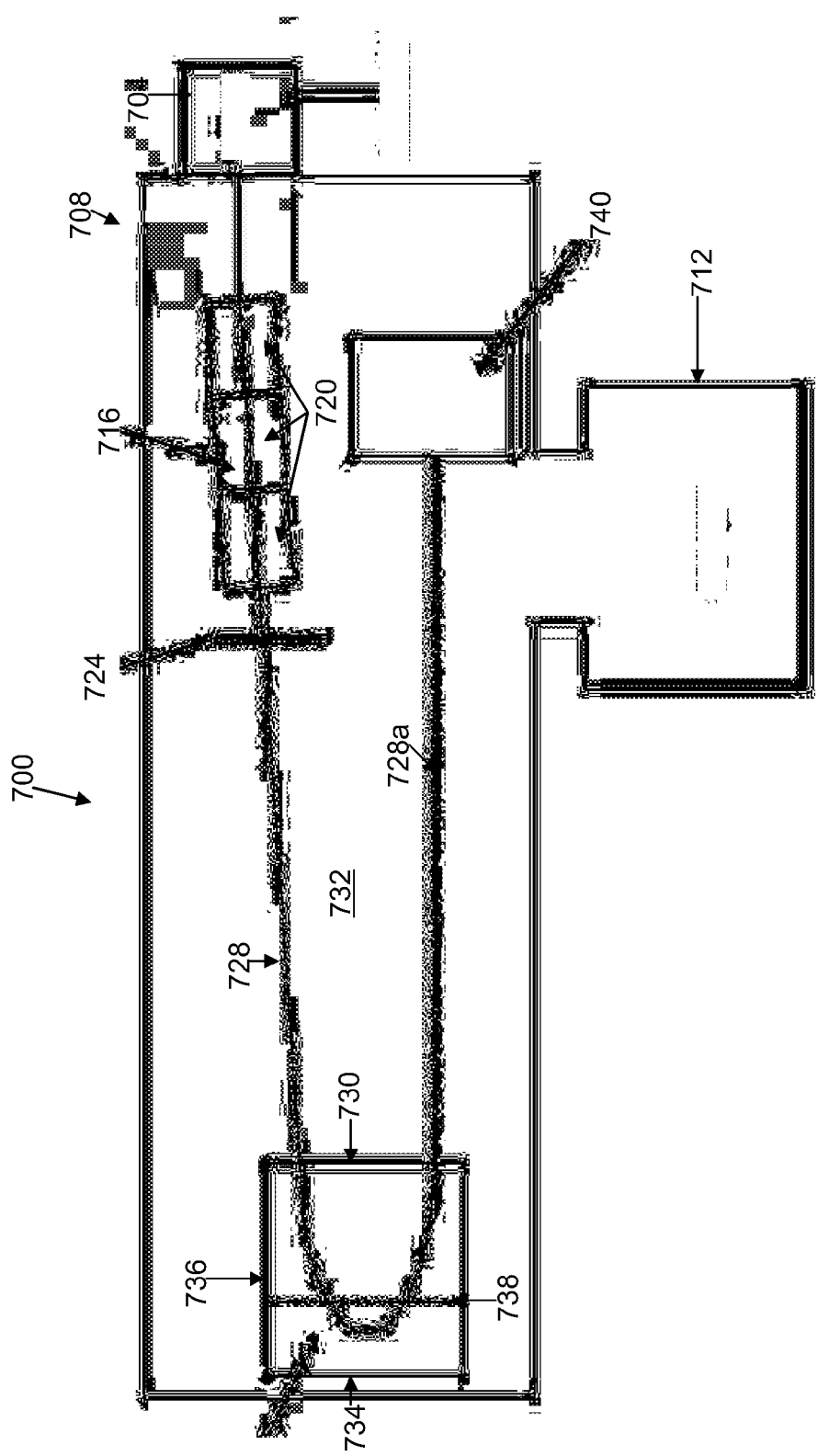
FIG. 7 is a plan view of a time-of-flight mass spectrometer module that embodies the invention.

FIG. 7 is a plan view of a time-of-flight mass spectrometer system 700 that embodies the invention. The system 700 includes an ion source 704 for supplying ions to the system 700. The ion source 704 can supply product ions and reagent ions from, for example, the chemical ionization/drift chamber 620 of the chemical ionization/drift region 508. Ions are passed from the ion source 704 into the time-of-flight mass spectrometer 708 via an ion flow. Ions can enter the time-of-flight mass spectrometer 708 through an ion extraction orifice (not shown) in an ion extraction electrode (not shown) that is electrically isolated from the time-of-flight mass spectrometer 708. An electric potential can be applied to the ion extraction electrode to generate an electromagnetic field for directing the ions within the time-of-flight mass spectrometer 708.

The time-of-flight mass spectrometer 708 is coupled in fluid communication with a pumping system 712 that establishes the pressure within the flight chamber 708. Ions are directed towards an ion optics assembly 716 that includes a set of ion lenses 720. One or more electrical potentials are applied to the ion lenses 720 to provide electromagnetic fields that direct and define the geometry of the ion beam. For example, the ion lenses 720 can constrain the possible trajectory of the ion flow and thereby focus the ion flow or increase the ion flux through a smaller volume. The ion lenses 720 can also reduce variability in a velocity spectrum or distribution of the ions. In some embodiments, the ion lenses 720 are electrostatic lenses, such as quadrupole lenses with one or more DC potentials applied. The ion lenses 720 generate a focusing field that interacts with the ion flow to minimize spatial variability in the direction of ion flow (e.g., along the trajectory 728). The optical assembly 716 can optimize characteristics of an ion beam or flow for, for example, increasing ion flux, momentum, or velocity of the ion flow. Such improvements in beam characteristics permit improved resolution of the mass spectrum and improved detection of peaks in the mass spectrum. Peaks in the mass spectrum are indicative of the identity or quantity of particular ions having a particular mass value. Improved resolution of the mass spectrum and spectral peaks allows improved differentiation between peaks and the spectrum or signal noise.

Ions exit the optical assembly 716 in a concentrated flow directed towards an ion beam adjuster 724. The ion beam adjuster 724 can be a chopper assembly that interrupts or modulates the flow of ions along a trajectory 728 through the flight region 732. In some embodiments, the ion beam adjuster 724 is coupled to a driving system (not shown), for example a digital electronics control module that controls parameters of the ion beam adjuster 724. The parameters can be controlled according to a specified interruption or flow pattern. Such parameters include positive and negative voltages which are applied to alternate wires in the ion beam adjuster, which results in ion scattering when the voltages are applied and which results in uninterrupted flow (or pulsing) of ions along the trajectory 728 when no potential is applied. In some embodiments, the magnitude of the applied positive and negative voltages can be adjusted for optimum performance. In some embodiments, the driving system controls parameters of the ion beam adjuster 724 according to a specified pattern, e.g., repeated opening and closing of the ion beam adjuster gate with a particular time period. The driving system can also control parameters of the ion beam adjuster 724 according to a random or unspecified pattern. In some embodiments, the driving system is based on a pseudo random binary sequence that can generate a pulsed flow of ions along the trajectory 728. In some embodiments, the ion beam adjuster 724 is an ion gate that can be rapidly switched to generate a pulsed ion flow, e.g., according to a specified flow pattern. An example of a suitable ion gate is known as a Bradbury-Nielsen gate.

The ions move along the trajectory 728 in the decreasing direction of the x-axis and towards a second optical system 736. The optical system 736 can be a reflectron (also referred to herein as 736) that affects and/or changes the direction of the trajectory 728 by reflecting ions, where the path of trajectory 728a is symmetrical with path of trajectory 728, with the axis of symmetry passing through the center of the reflectron 736. In some embodiments, the reflectron 736 includes a set of electrostatic lenses (not shown) to reflect and/or redirect the flow of ions along the reflected trajectory 728a. In some embodiments, the reflectron 736 consists of two sections of a resistive glass tube that are bonded together. A grid (not shown) is located at the front face 730 of the reflectron 736 and a second grid 738 is positioned between the two bonded tube sections. Fixed electrical potentials can be applied to the grid at the front face 730, at the grid between the two sections of tube, and at the rear face 734 of the reflectron 736. Such a configuration allows an electrical field gradient to be established within the tube for ion reflection. After exiting the optical system 736, the ions follow the reflected trajectory 728a to a detector 740.

The optical system 736 can be used to increase the path length, l, over which the ions travel in the flight region 732, for example, to increase resolution of signal peaks in the acquired mass spectrum. The path length, l, can have a known or determined value based on, for example, the sum of the length of each of the trajectory 728 and the reflected trajectory 728a. The amount of time required by ions to traverse the path length, l, can be used to determine the mass or mass-to-charge ratio for the reagent ions or the product ions. For example, the amount of time required to traverse the path length, l, is indicative of the velocity or kinetic energy of the ion in the flight chamber 708, after acceleration under the influence of the electromagnetic field generated by the optical system 716. The time an ion spends traversing the path length l can be used with the Lorentz force law and Newton's second law to determine mass or mass-to-charge ratio. The optical system 736 can also be used to correct for variations in the kinetic energy of the reagent ions and the product ions. Ions having a relatively higher kinetic energy travel further into the optical system (along the decreasing x-axis) than ions with relatively lower kinetic energy. This phenomenon is sometimes referred to as penetration or reflectron penetration. Positioning the detector 740 at or near a focal point of the trajectory 728 or reflected trajectory 728a reduces effects of energy distribution on the mass spectrum.

Ions moving through the flight region 732 from different pulses of the ion beam adjuster 724 can mix in the flight region 732, causing signal convolution, either in the signal received by the detector 740 or in the mass spectrum generated by the detector 740. The detector 740 is generally positioned at or near an energy focal point such that ions of the same mass but with differing energies exiting the optical system 736 are collected by the detector approximately simultaneously. In some embodiments, the detector 740 is a stacked micro-channel plate-type detector. The detector 740 operates in pulse counting mode. Pulse counting mode permits collection of individual ions as they arrive at the detector, after passing through the flight region 732. In some embodiments, the detector 740 is used in conjunction with a signal discriminator, an amplifier and/or a time-to-digital converter (TDC).

When the ion beam adjuster 724 employs pseudo random binary sequence-type pulsing, the signal acquired from ions collected by the detector 740 can be deconvoluted using signal processing techniques, such as statistical signal processing techniques. Statistical signal processing techniques provide information about a signal or spectrum based on a statistical analysis of the convoluted signal or spectrum. An example of a suitable signal processing technique for deconvoluting the acquired signal is maximum likelihood signal processing.

Maximum likelihood signal processing typically performs statistical computations based on measured events. For example, for a collection of N events measuring an independent variable $x_i$ and a dependent variable $y_i$ with i from 1 to N, a fitting function can be determined from the measured data $x_i$ and $y_i$. The fitting function will include m parameters, $a_i$, with i from 1 to m. The fitting function can be written for each event in the form of $y(x_i) \equiv y(x_i; a_1, a_2, \ldots, a_m)$. For each event, the $y(x_i)$ fitting function can be converted to a normalized probability density function $P_i \equiv (x_i; a_1, a_2, \ldots, a_m)$. The probability density function P, can be calculated at the observed value of $x_i$. A likelihood function $L(a_1, a_2, \ldots, a_m)$ is the product of the individual probability densities such that $$L(a_1, a_2, \ldots, a_m) = \prod_{i=1}^{N} P_i,$$

and the maximum likelihood values of the various parameters $a_i$ can be obtained by minimizing the likelihood function $L(a_1, a_2, \ldots, a_m)$ with respect to the parameters.

In some embodiments, the time-of-flight mass spectrometer 700 is operated using pseudo random binary sequence pulsing of the ion beam adjuster 724 to produce a convoluted signal or spectrum. The convoluted signal or spectrum is then deconvoluted using maximum likelihood signal processing. When used in this mode, the ion beam adjuster 724 allows ions to pass for approximately 50% of the total available time, allowing approximately 50% of the total available ions to pass through the flight region 732. This "high duty cycle" operation of the time-of-flight mass spectrometer provides performance benefits in terms of enhanced signal-to-noise, improved sensitivity and wider dynamic range. In some embodiments, the time-of-flight mass spectrometer 700 is operated in single pulse mode where all ions from a single pulse of the ion beam adjuster 724 are collected by the detector 740 before a subsequent pulse of the ion beam adjuster is triggered.

In addition to the benefits provided by "high duty cycle" operation of the time-of flight mass spectrometer 700, maximum likelihood signal processing also provides additional performance improvements over other signal deconvolution methods. Maximum likelihood signal processing treats signal noise as Poisson noise rather than Gaussian noise. Maximum likelihood signal processing can also reference actual instrument response functions, for example the actual ion beam adjuster pulse shape, rather than an idealized instrument response function. These performance improvements facilitate increased signal resolution, as well as further enhancements in signal-to-noise and dynamic range.

In some embodiments, the maximum likelihood signal processing is performed by a data analysis module (not shown). The data analysis module can also be used to identify species in the mass spectrum, for example, based on a look-up table or univariate or multivariate probabilistic methods. In some embodiments, the data analysis module can be based on a multivariate statistical analysis. Examples of suitable multivariate statistical analyses include, for example, partial least squares discriminant analysis (PLS-DA) or principal component analysis using a Hotelling-type analysis or a DModX-type analysis. In some embodiments, the data analysis module is used to interpret sample data to determine if a sample is associated with a particular population. In some embodiments, the data analysis module monitors the diagnostic output of a system to determine whether a fault has occurred in the system, e.g., the system 100 of FIG. 1.

Many applications for the mass spectrometry systems and techniques described herein exist. In particular, volatile organic compounds in trace quantities or concentrations can be detected. The increased sensitivity and ability to detect and identify trace volatile organic compounds in real-time provides a variety of applications for the systems and methods herein. Particular applications include sampling of gas (e.g., environmental air, gas from an enclosed space, gas from a gas supply, gas emitted from a solid sample or from a container or in the head space above a food or beverage product). The sampled gas is then introduced to a gas sample inlet port and interacted with reagent ions to form product ions. The particular application and detection of volatile organic compounds is related to how and where the gas sample inlet port is positioned.

In some embodiments, the gas sample inlet port includes application specific features to tailor the gas sample inlet port to the needs of the application. For example, in medical diagnostics applications, the gas sample inlet port may be coupled to a face mask covering the nose and mouth of a person. The gas sample inlet port or the face mask also can incorporate a bacterial filter. In applications involving sampling from an environment containing particles, a particle filter may be incorporated into, for example, the sample line or gas sample inlet port. In applications where the sample vapor contains species that may condense, a heater may be incorporated into the system (e.g., the sample line) to heat the sample line to a specific temperature.

Examples of sample gas collectors include containers, canisters, or vacuum-based products that contain an outlet port for gas to pass into the gas sample inlet port. A gas collector can collect gas in the environment in which the gas is found and store the gas for later analysis, in which case the collector is relatively gas impermeable. In some embodiments, the gas collector includes an outlet port that feeds into a gas sample inlet port and into the drift chamber for real-time detection and/or monitoring.

The various applications for the mass spectrometry system and methods described hereafter are within the scope and spirit of the invention. One category of applications for the described mass spectrometry techniques involves measurement of trace-level concentrations of volatile organic compounds in air, including environmental air. Environmental air can be sampled from enclosed spaces or non-enclosed spaces (e.g., by positioning a gas sample inlet port in proximity to the environmental air).

Volatile organic compounds can be monitored in urban areas for detection of vehicle emissions or pollutants within cities and towns and/or in proximity to industrial sites. These are sometimes referred to as anthropogenic VOCs. For example, industrial sites can include chemical factories, waste incineration plants, steel and/or cement production facilities. Industrial facilities may emit VOCs such as dioxin surrogates (and dioxin-based compounds), furans (and furan-based compounds), chlorophenols, naphthalene, benzene, toluene, ethylene, xyethylene (collectively BTEX) species. Moreover, VOCs or urban hazardous air pollutants identified by regulatory agencies, such as the Environmental Protection Agency in the U.S. or Ministry for the Environment (MfE) in other countries, in response to particular programs such as VOC initiatives or non-methane organic compound initiatives.

In some embodiments, positioning a gas sample inlet port near a waste incineration plant or smokestack is useful for real-time monitoring and adjustment (e.g., real-time feedback) to reduce emissions. Such real-time monitoring is also useful for confirming the stated efficiency of scrubbers and to optimize combustion processes.

In some embodiments, a gas sample inlet port is positioned in an enclosed space for monitoring VOC content in the air in the enclosed space. Examples of enclosed spaces include within buildings, within vehicles and in aircraft cabins. Gas can be sampled from workspace locations (e.g., clean rooms in semiconductor fabrication facilities or foundries) to confirm adherence to environmental regulations (e.g., occupational safety and health regulations). Gas sample inlet ports can also be used for real-time monitoring and detection of air handling and filtration systems in buildings for ambient air control, for investigating "sick building" syndrome, detecting degradation of building materials including in leaking buildings, and testing consumer products within buildings (e.g., fumes emitted by coatings and materials).

The mass spectrometry described herein can be used to monitor and detect VOCs emitted by forests and/or plants, for example, in non-urban, rural, or remote locations. Typically, this type of VOC is known as a "biogenic" VOC. In some embodiments, gas is sampled from the headspace of a vessel containing a soil sample (e.g., to test for VOC's in soil samples taken from or around a contaminated site). The mass spectrometry techniques can be used to monitor, detect, and analyze gases emitted by landfill sites, livestock farming zones (including concentrated animal feeding operations), and/or water systems.

In non-enclosed spaces, a gas sample inlet port can be positioned downstream from an automobile or aircraft engine exhaust to monitor and/or quantify VOC content of such emissions or other gasses of interest, including hydrogen sulfide ($H_2S$). The techniques described herein are also applicable in the study of atmospheric chemistry and/or atmospheric composition by positioning a gas sample inlet port to acquire atmospheric gasses. Such gasses are analyzed to study and evaluate photo-oxidation processes and/or other mechanisms leading to the formation of secondary organic aerosols that can include isobaric compounds.

The techniques described herein are also applicable to the food and beverage industries. For example, the head-space above a food or beverage product contains gasses that can be analyzed using mass spectrometry. The head-space can be in an enclosed space (e.g., within a sealed container) or in a non-enclosed space.

Examples of food and beverage applications include monitoring, identifying, and grouping flavors and/or aromas in a variety of foodstuffs such as, for example, coffee, olive oil, dairy products, meat products (including poultry and pork), fish products, herbs and spices, beer, wine, and other alcoholic beverages. Flavors in gasses can be determined and/or identified based on VOC components that contribute to different flavors. Chemical ionization reaction and/or proton transfer reaction mass spectrometry can be used to monitor food spoilage and/or decay, for example, through analysis of VOCs produced as a result of bacterial activity in the food. The mass spectrometry herein can be used to determine freshness of food (e.g., bread), and provide quality assurance and quality control, as well as helping determine product stability and shelf life. Mass spectrometry techniques can be used in process monitoring for food production, including mixing, blending, roasting, and cooking and to determine whether a particular batch of food is unsuitable for distribution or consumption.

Within the food and beverage industry, mass spectrometry can be used to detect contamination in food from the food packaging (e.g., solvent residue or contaminants from plastic food packaging). The mass spectrometry techniques herein have applicability in testing water-soluble and fat-soluble antioxidants and/or other food additives that are used in various foods.

Chemical ionization reaction and/or proton transfer reaction mass spectrometers also have applications in the medical and healthcare fields as instruments for diagnostics or prognostics. For example, a gas sample inlet port can be positioned in proximity to a human mouth to collect human breath to provide to the mass spectrometry system. VOCs in breath can indicate presence of particular diseases or physical conditions within a patient. Several examples of applications of breath analysis involving VOCs exist. For example, breath can be analyzed to screen for various types of cancer, e.g., lung cancer, by detecting particular alkanes or benzene derivatives. Breath can also be analyzed for other conditions such as tuberculosis, diabetes, fungal infections (e.g., in bone marrow patients), schizophrenia, and/or bipolar disorders based on the VOC species and quantities thereof in a patient's breath.

The mass spectrometry described herein can also be used to monitor kidney or other renal functions. Human breath of cystic fibrosis sufferers can include specific VOCs when a bacterial infection is present, and the infection can be diagnosed. In some embodiments, human breath includes specific VOCs indicative of organ transplant rejection. Human breath can also include, in trace concentrations, performance enhancing drugs that can be detected by the spectrometry described. Breath analysis and detection of VOCs can also be used to tailor a diet and training regimen for athletes and patients. The analysis of VOC's on human breath, using the mass spectrometers described herein, enables the evaluation and monitoring of metabolic function, and diagnosis of thyroid problems.

Chemical ionization reaction and/or proton transfer reaction mass spectrometry have applications in the field of security, bio-security, forensic science, and criminal investigation. For example, the systems and methods described here in can be used to monitor and detect explosive materials, Chemical Warfare Agents (CWAs) and/or battlefield gasses, fire accelerants (in arson investigations), and the location of buried bodies. Moreover, a gas sample inlet port can be positioned to collect human breath to screen for exposure to CWAs or battlefield gasses. Mass spectrometry can be used to detect and analyze the specific VOC's which are characteristic of different bodily fluids (e.g., evidence collected at a crime scene). The concepts described herein are also applicable to screening and detecting narcotics and/or drugs of abuse, either via breath analysis, or by coupling a gas sample inlet port to a container suspected of containing drugs. More generally, a gas sample inlet port can be coupled to a shipping container or package to detect VOC's that are characteristic of materials or substances that pose a bio-security threat (e.g., anthrax or spores).

The techniques described can also be used to monitor crops for agricultural pest and pathogen contamination, evidenced by the presence of VOCs. For example, a gas sample inlet port can be positioned near grain to detect the presence of a fungal toxin (mycotoxins) in the grain. Chemical ionization reaction and/or proton transfer reaction mass spectrometry can also be used to detect fungi or insects in post-harvested crops (e.g., before distribution to food and beverage production companies).

Chemical ionization reaction and/or proton transfer reaction mass spectrometry applications also exist in the cosmetics, toiletries, and consumer pharmaceutical industries, such as, for example, analysis and testing of products during product development phase. Mass spectrometry can also be employed during the production process to detect any faults or defective products before distribution.

Examples of applications from the cosmetic, toiletries, and consumer pharmaceutical industries include fragrance research and development based on the identification of VOC components that contribute to particular fragrances (e.g., perfumes, antiperspirants, and deodorants). The concepts described here are also applicable to development and testing of toiletries and consumer products (e.g., to monitor VOC content and detect VOC levels during use in testing or in the laboratory environment). Such products include mouthwash, toothpaste, soaps, antiseptic ointments and creams, deodorants, and antiperspirants. Oral hygiene products can also be analyzed and monitored using breath analysis. Like the food and beverage industry, chemical ionization reaction and/or proton transfer reaction mass spectrometry can be used for general quality control and/or quality assurance programs for cosmetics, toiletries, and consumer pharmaceutical products, including assessment of product stability and/or shelf life.

Additional applications for chemical ionization reaction and/or proton transfer reaction mass spectrometry exist. For example, the concepts described can be used in process monitoring and control in the biopharmaceutical industry, for example, monitoring and identifying VOCs produced during a fermentation process. Certain regulatory authorities (e.g., ASTM International) have promulgated objectives to improve the quality, safety, and efficiency of biopharmaceutical product manufacture. Positioning a gas sample inlet port to collect sample for on-line analysis during the manufacturing process can further those regulatory goals.

In some embodiments, mass spectrometry can be used for biological research purposes, to detect VOCs in trace concentrations associated with plant leaf wounding and defense mechanisms. In some embodiments, a gas sample inlet port is positioned to collect sample from a gas supply, e.g., a hydrocarbon plume. The VOC content of the gas supply is determined according to the methods described above. A hydrocarbon plume can be indicative of oil and/or gas deposits, and the mass spectrometry techniques herein can be used in petroleum exploration. Chemical ionization reaction and/or proton transfer reaction mass spectrometry can also be used in analysis and optimization of catalyst performance in the automotive industry. In such applications, a gas sample inlet port is positioned to collect both pre- and post-catalyst gas species, e.g., for comparison purposes. Other applications will be apparent to those of skill, and are within the scope and spirit of the invention.

In some embodiments, spectrometers incorporating principles of the invention are used as a component of an electronic nose system. In some embodiments, the electronic nose system also includes an analysis module for analyzing signals output by the spectrometer. Electronic nose systems can be used to analyze vapors and gases, including those in the headspace above solid or liquid substances, which include a plurality of components. The analysis module analyzes the signals output by the spectrometer and is able to identify the specific components in the sample. Moreover, the analysis module performs a global fingerprint analysis of the species present (i.e., acquires a chemical signature) which is compared with fingerprints from other substances in previously stored information.

In some embodiments, the analysis module includes a computer processor that implements, for example, a multivariate analysis algorithm, pattern recognition algorithm or neural network algorithm which are particularly useful for processing a large number of sample parameters (e.g., the many VOC component peaks that are characteristic of certain odors and flavors) to characterize and compare samples. For example, a multivariate analysis technique is useful for observation and analysis of more than one statistical variable and can reduce the data from a complex fingerprint to enable simple comparisons to be made. Using this approach, similar flavors and odors can be grouped and outliers can be identified and highlighted.

Electronic nose systems have been used in analyzing the global fingerprints of VOC's emitted by foods and beverages, which often are composed of a large number of components (e.g., a plurality of different VOC species). For example, an odor is composed of molecules, each of which has a specific size and shape. Each of the molecules has a correspondingly sized and shaped receptor in the human nose. A spectrometer can be used to uniquely fingerprint the many different molecules within the odor sample. Additional applications for electronic nose systems includes detection of odors specific to diseases for medical diagnosis, and detection of pollutants and gas leaks for environmental protection. In some embodiments, the electronic nose system includes additional sensors (e.g., one or more gas sensors, including metal oxide semiconductor (MOS), conducting polymer (CP), quartz crystal microbalance and field effect transistor (MOSFET) sensors) that output signals that are analyzed by the analysis module.

While the invention has been particularly shown and described with reference to specific embodiments, it should be understood by those skilled in the art that various changes in form and detail may be made therein without departing from the spirit and scope of the invention as defined by the appended claims.

What is claimed is:

1. A method comprising:
   introducing a non-ionized sample gas;
   supplying a reagent vapor to a plasma chamber;
   generating one or more reagent ions from the reagent vapor supply in the plasma chamber by transferring microwave or high-frequency RF energy from a cavity to the plasma chamber to form one or more reagent ions;
   directing the one or more reagent ions to a drift chamber;
   reducing an amount of microwave or high-frequency RF energy extending into the drift chamber from the plasma chamber;
   interacting the one or more reagent ions with the non-ionized sample gas to form one or more product ions;
   directing the one or more product ions and the one or more reagent ions to a quadrupole or time-of-flight mass spectrometer module; and
   determining by the mass spectrometer module a value for at least one of a peak intensity or mass of each of the one or more product ions and the one or more reagent ions.

2. The method of claim 1, wherein the non-ionized sample gas includes one or more volatile organic compounds in at least a trace concentration.

3. The method of claim 1, wherein introducing comprises coupling a gas sample inlet port to an enclosed space.

4. The method of claim 1, wherein introducing comprises positioning a gas sample inlet port in a non-enclosed space.

5. The method of claim 1, wherein introducing comprises coupling a gas sample inlet port to a container.

6. The method of claim 1, wherein introducing comprises coupling a gas sample inlet port downstream from an exhaust of an automobile or aircraft.

7. The method of claim 1, wherein introducing comprises coupling a gas sample inlet port to a head-space above a food or beverage product.

8. The method of claim 1, wherein introducing comprises positioning a gas sample inlet port in proximity to a human mouth to collect exhaled breath.

9. The method of claim 1, wherein introducing comprises positioning a gas sample inlet port in proximity to a solid sample material emitting a gas or vapor.

10. The method of claim 1, wherein introducing comprises coupling a gas sample inlet port to a supply of gas.

11. The method of claim 1, wherein reducing an amount of microwave or high-frequency RF energy further comprises positioning a choke between the plasma chamber and the drift chamber.

* * * * *